United States Patent [19]

Rogers et al.

[11] Patent Number: 4,861,788

[45] Date of Patent: Aug. 29, 1989

[54] ANTIBACTERIAL 1-NORMON-2-YL-HETEROCYCLIC COMPOUNDS

[75] Inventors: Norman H. Rogers, Horsham; Graham Walker, Guildford; Michael J. Crimmin, Horsham; Peter J. O'Hanlon, Redhill, all of England

[73] Assignee: Beecham Group plc, Middlesex, England

[21] Appl. No.: 8,893

[22] Filed: Jan. 30, 1987

Related U.S. Application Data

[63] Continuation of Ser. No. 582,832, Feb. 23, 1984, abandoned.

[30] Foreign Application Priority Data

Feb. 25, 1983 [GB] United Kingdom ............... 8305316

[51] Int. Cl.$^4$ ................... A61K 31/41; C07D 417/14; C07D 413/14
[52] U.S. Cl. .................................. 514/364; 514/361; 514/362; 514/363; 548/127; 548/128; 548/131; 548/136; 548/143; 548/250; 549/417
[58] Field of Search ............... 548/131, 143, 127, 128, 548/136; 514/361, 362, 363, 364

[56] References Cited

U.S. PATENT DOCUMENTS 4,812,470  3/1989  Rogers et al. ................ 514/365

FOREIGN PATENT DOCUMENTS 1914    5/1979  European Pat. Off. .
87953   9/1983  European Pat. Off. .

Primary Examiner—Cecilia Shen
Attorney, Agent, or Firm—Hopgood, Calimafde, Kalil, Blaustein & Judlowe

[57] ABSTRACT

Compounds of formula (I):

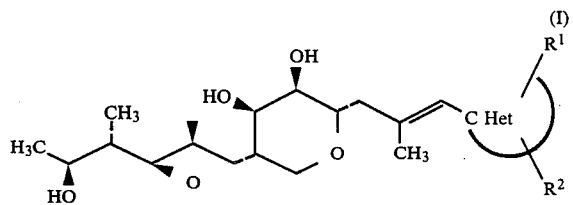

wherein

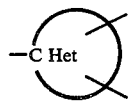

is a 5-membered heterocyclic group having a 6-$\pi$ electron system, the five ring atoms being either
(a) one carbon atom and four atoms selected from carbon and nitrogen,
(b) two carbon atoms, two nitrogen atoms and one atom selected from oxygen and sulphur, or
(c) four carbon atoms and one atom selected from oxygen and sulphur
and $R^1$ is a substituent on a carbon or nitrogen of

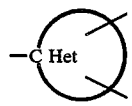

selected from $C_{1-20}$ alkyl, $C_{2-8}$ alkenyl aryl, aralkyl and heterocyclyl, each of which may optionally be substituted; hydrogen and $C_{3-7}$ cycloalkyl,
and, where appropriate, $R^2$ is a substituent on a carbon or nitrogen of

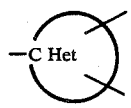

and when present is the same or different to $R^1$ and is selected from $C_{1-20}$ alkyl, $C_{2-8}$ alkenyl, aryl, aralkyl and heterocyclyl each of which may optionally be substituted; hydrogen and $C_{3-7}$ cycloalkyl, have antibacterial and antimycoplasmal activity.

7 Claims, No Drawings

ANTIBACTERIAL 1-NORMON-2-YL-HETEROCYCLIC COMPOUNDS

The present invention relates to compounds having antibacterial and/or antimycoplasmal activity, to a process for their production and to their use in human and veterinary medicine.

Accordingly the present invention provides a compound of formula (I):

(I)

wherein $$-C\overset{/}{\underset{\diagdown}{\text{Het}}}$$

is a trivalent, 5-membered heterocyclic group having a 6-π electron system, the five ring atoms being either
(a) one carbon atom and four atoms selected from carbon and nitrogen,
(b) two carbon atoms, two nitrogen atoms and one atom selected from oxygen and sulphur, or
(c) four carbon atoms and one atom selected from oxygen aand sulphur and $R^1$ is a substituent on a carbon or nitrogen of $$-C\overset{/}{\underset{\diagdown}{\text{Het}}}$$

selected from $C_{1-20}$ alkyl, $C_{2-8}$ alkenyl aryl, aralkyl and heterocyclyl, each of which may optionally be substituted; hydrogen and $C_{3-7}$ cycloalkyl, and, where appropriate, $R^2$ is a substituent on a carbon or nitrogen of $$-C\overset{/}{\underset{\diagdown}{\text{Het}}}$$

and when present is the same or different to $R^1$ and is selected from $C_{1-20}$ alkyl, $C_{2-8}$ alkenyl, aryl, aralkyl and heterocyclyl each of which may optionally be substituted; hydrogen and $C_{3-7}$ cycloalkyl.

Suitable aryl groups include phenyl groups.

Suitable aralkyl groups include those wherein the aryl moiety is a phenyl group and those wherein the alkylene radical has from 1 to 4 carbon atoms.

Suitable heterocyclyl groups include those having 5 or 6 members in the heterocyclic ring and containing from 1 to 3 heteroatoms each selected from oxygen, nitrogen and sulphur.

Suitable substituents for a phenyl and heterocyclyl groups include halogen, $C_{1-6}$ alkyl, $C_{1-6}$ alkoxy, hydroxy, carboxy, $C_{1-6}$ alkoxycarbonyl, carbamoyl, mono- or di-($C_{1-6}$)alkyl carbamoyl, sulphamoyl, mono- and di-($C_{1-6}$)alkylsulphamoyl, cyano, nitro, amino, mono- and di-($C_{1-6}$)alkylamino, $C_{1-6}$ acylamino, ureido, $C_{1-6}$ alkoxycarbonylamino, 2,2,2-trichloroethoxycarbonylamino, $C_{1-6}$ alkanoyl, $C_{1-6}$ alkylthio, $C_{1-6}$ alkanesulphinyl, and $C_{1-6}$ alkanesulphonyl.

Suitable substituents for alkyl, alkenyl and alkynyl groups include halogen, carboxy, $C_{1-6}$ alkoxycarbonyl, carbamoyl, mono- or di-($C_{1-6}$)alkylcarbamoyl, sulphamoyl, mono- and di-($C_{1-6}$)-alkylsulphamoyl, amino, mono- and di-($C_{1-6}$)alkylamino, $C_{1-6}$ acylamino, ureido, $C_{1-6}$ alkoxycarbonylamino, 2,2,2-trichloroethoxycarbonylamino, aryl, heterocyclyl, hydroxy, $C_{1-6}$ alkoxy, oxo, aroyl, 2-thenoyl, $C_{1-6}$ alkylthio, $C_{1-6}$ alkanesulphinyl, $C_{1-6}$ alkanesulphonyl, hydroxyimino, hydrazono, benzohydroximoyl, 2-thiophenecarbohydroximoyl.

Compounds of formula (I) have a tri-substituted double bond and this may be in either the E or Z configuration giving rise to two geometrically isomeric forms. The present invention encompasses both such isomers individually and admixed in any proportions. In general, greater biological activity is associated with the E isomer and for this reason the E isomer is preferred.

Compounds of formula (I) having the E configuration have been named '1-normon-2-yl-heterocycles'. The absolute stereochemistry of the 1-normon-2-yl radical is as shown in formula (I).

It will be appreciated that $$-C\overset{/}{\underset{\diagdown}{\text{Het}}}$$

represents the residues of a variety of related heterocyclic systems including:

(a) pyrroles diazoles triazoles tetrazoles

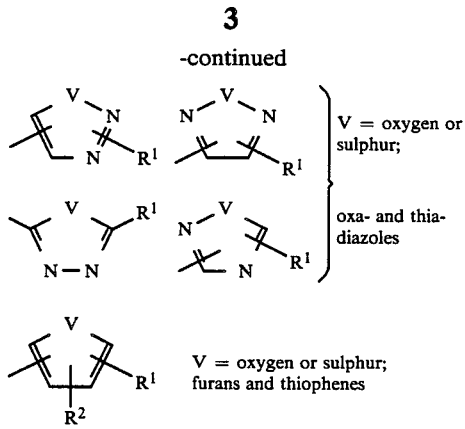

V = oxygen or sulphur;

oxa- and thia-diazoles (b)

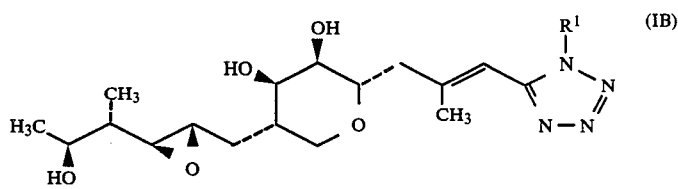

(IA)

wherein R¹ is as defined in relation to compounds of formula (I).

A second preferred sub-group of compounds within formula (I) are the compounds (IB):

(c)

V = oxygen or sulphur; furans and thiophenes

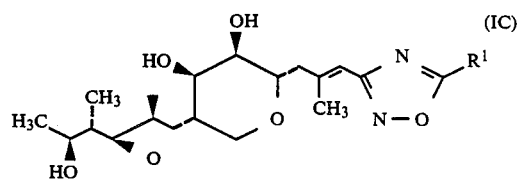

(IB)

wherein R¹ is as defined in relation to compounds of formula (I).

A third preferred sub-group of compounds within formula (I) are the compounds of formula (IC)

All these are encompassed by the invention. It will be appreciated that for the tetrazoles, oxa- and thiadiazoles that it is not possible for there to be a substituent R².

Preferably

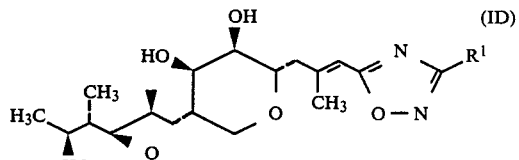

(IC)

wherein R¹ is as defined in relation to compounds of formula (I).

A fourth preferred sub-group of compounds within formula (I) are the compounds of formula (ID)

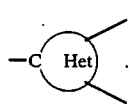

is a substituted oxadiazolyl moiety, especially a substituted 1,3,4-oxadiazolyl moiety.

Preferably the 1-normon-2-yl moiety is bonded to a carbon atom which itself is bonded to a heteroatom of

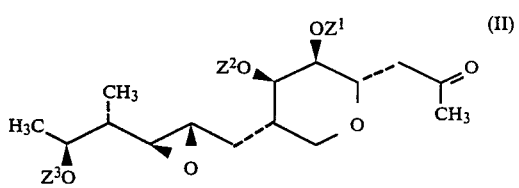

(ID)

wherein R¹ is as defined in relation to compounds of formula (I).

The present invention provides a process for producing a compound of formula (I) which process comprises reacting a compound of formula (II):

Preferably the heteroatom is nitrogen. More preferably the carbon atom is bonded to two heteroatoms one of which is nitrogen.

Preferably R¹ is bonded to an atom located in the β-position in relation to the carbon atom of

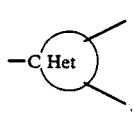

to which the 1-normon-2-yl moiety is bonded.

A preferred sub-group of compounds within formula (I) are the compounds of formula (IA):

(II)

wherein Z¹, Z² and Z³ are the same or different and each is hydrogen or a hydroxyl-protecting group with a compound of formula (III):

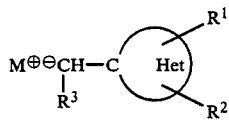
(III)

wherein R¹ and R² are as defined in relation to compounds of formula (I)

M⁺ is a metal cation, preferably an alkali metal cation, most preferably a lithium or sodium cation, and R³ is an anion-stabilising group which will spontaneously eliminate with a β-hydroxyl group to produce an olefin, preferably a trialkylsilyl or a dialkylphosphonate group, most preferably trimethylsilyl or diethylphosphonate, and, where necessary, removing any hydroxyl-protecting groups, and, if desired, converting one compound of formula (I) into a further compound of formula (I).

The present invention also provides a process for producing a compound of formula (IA) which process comprises cyclising a compound of formula (IV):

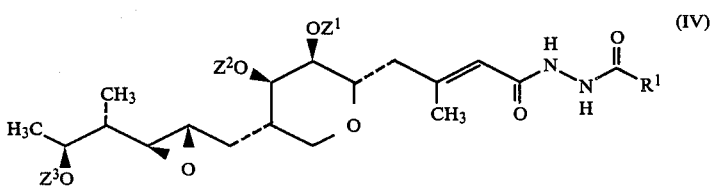
(IV)

wherein R¹ is as defined in relation to compounds of formula (I): and

Z¹, Z² and Z³ are the same or different and each is hydrogen or a hydroxyl-protecting group to form a compound of formula (IA)

and, where necessary, removing any hydroxyl-protecting groups, and, if desired, converting one compound of formula (IA) into a further compound of formula (IA).

The present invention also provides a process for producing a compound of formula (IB) which process comprises reacting a compound of formula (V)

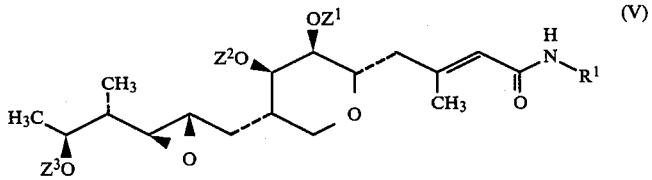
(V)

wherein R¹ is as defined in relation to compounds of formula (I) and Z¹, Z² and Z³ are the same or different and each is hydrogen or a hydroxyl-protecting group with phosgene and a tertiary amine and then with tetramethylguanidinium azide, and, where necessary, removing any hydroxyl-protecting groups and, if desired, converting one compound of formula (IB) into a further compound of formula (IB).

The present invention also provides a process for producing a compound of formula (ID) which process comprises cyclising a compound of formula (VI)

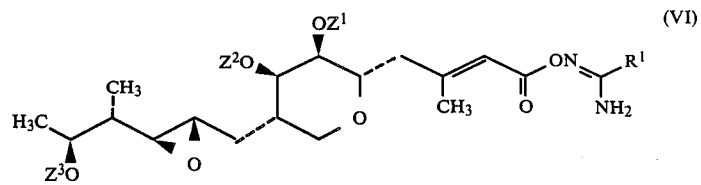
(VI)

wherein R¹ is as defined in relation to compounds of formula (I) and Z¹, Z² and Z³ are the same or different and each is hydrogen or a hydroxyl-protecting group and, where necessary, removing any hychoryl-protecting groups and, if desired converting one compound of formula (IB) into a further compound of formula (IB).

The reaction of a compound of formula (II) with a compound of formula (III) may conveniently be effected in an organic solvent, such as tetrahyrofuran, diethyl ether or dimethyl sulphoxide, at reduced or elevated temperature, such as from −80° to 100° C.

The cyclisation of a compound of formula (IV) is suitably effected using a chlorinating agent such as phosphorus oxychloride, phosgene, thionyl chloride or phosphorus pentachloride in the presence of a tertiary amine, such as triethylamine or pyridine. Such reactions are conveniently effected in an organic solvent, for instance dichloromethane or tetrahydrofuran, at ambient or reduced temperature, for instance −80° C. to 100° C., over a period of several hours to a few days. Preferably phosgene or phosphorus oxychloride are used, at temperatures of from 0° to 20° C.

Alternatively, cyclisation may be effected using triphenylphosphine and carbon tetrachloride as the chlorinating reagent, in the presence of a tertiary amine, for instance triethylamine, in an inert solvent such as acetonitrile or acetonitrile-pyridine. This type of process is described by H. Vorbruggen and K. Krolikiewicz in Tet. Letts., 1981, 4471: it is particularly advantageous in that the production of compounds of formula (IV) and cyclisation of these to compounds of formula (IA) may be conducted in situ.

Compounds of formula (IV) may also be cyclised using a carboxylic anhydride or mixed anhydride or acid chloride, such as trifluoroacetic anhydride or trichloroacetic anhydride or trichloroacetyl chloride which latter is used in the presence of pyridine. In this reaction the hydroxy groups of the 1-normon-2-yl moiety become acylated and must subsequently be deprotected. When trifluoroacetic anhydride is used to effect the cyclisation the trifluoroacetyl groups may be removed using aqueous base such as potassium carbonate. Appropriate deprotecting conditions for removing other acyl residues will be readily apparent to the skilled person. Alternatively the hydroxy groups of the 1-normon-2-yl moiety may be protected, prior to cyclising with a carboxylic anhydride, and deprotected by conventional methods such as described below.

The reaction of a compound of formula (V) with phosgene and a tertiary amine is suitably effected at ambient or reduced temperature such as from −20° C. to 20° C., in the presence of a suitable solvent such as toluene. Preferably the tertiary amine is triethylamine. The subsequent reaction with tetramethylguanidinium azide is suitably effected at ambient temperature and may conveniently be conducted without separation or purification after the reaction with phosgene and a tertiary amine.

The cyclisation of a compound of formula (VI) is suitably effected by heating the compound in a suitable solvent under dehydrating conditions. Conveniently the compound of formula (VI) is heated in diglyme to a temperature above 100° C., for instance to about 150° C. Conversion of one compound of formula (I) to another compound of formula (I) may be effected by conventional methods. Thus, for instance, substituents on the group R¹ or R² may be modified or additional substituents may be inserted. Included within modification of the group R¹ or R² are salification and esterification of a carboxy substituent, trans- and de-esterification of an ester-containing substituent and formation of the free carboxy group from a carboxylate salt. Another example of such conversion is the formation of alkanesulphinyl and alkanesulphonyl compounds from the corresponding alkylthio compound of formula (I). This latter conversion may be achieved using conventional oxidising agents such as percarboylic acids, for instance m-chloroperbenzoic acid, in a suitable solvent.

The compound of formula (II) wherein $Z^1$, $Z^2$ and $Z^3$ are hydrogen, and processes for its production, are described in U.K. Pat. No. 1,587,060. Derivatives thereof wheren $Z^1$, $Z^2$ and $Z^3$ are hydroxyl protecting groups may be produced by conventional methods such as those mentioned below. When this compound is produced with hydroxyl protecting groups already in place it may be used directly or even in situ in the above reaction or it may be optionally deprotected and/or isolated.

The compounds of formula (III) may be produced by conventional processes such as those shown in Scheme I.

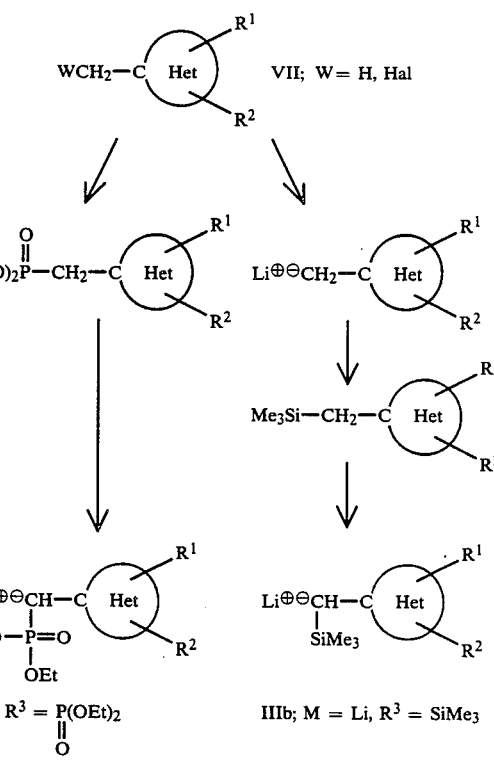

The starting materials of formula (VII) are either well known and readily available or may be produced by conventional processes. When

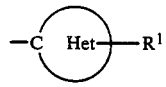

is a substituted 1,3,4-oxadiazolyl moiety, compounds of formula (VII) may be produced from compounds of formula (VIII):

by conventional methods. Suitable methods for producing compounds of formula (VII) are described in Elderfield, *Heterocyclic Compounds*, Vol 5 Chapter 5 and Vol 7 Chapter 6, and by C. Ainsworth, *J. Amer. Chem. Soc.*, produce compounds of formula (III) wherein $R^3$ is

are described by W. S. Wadsworth Jr., *Organic Reactions*, (1977), 25, 73. Analogous processes to those of the reaction sequence from compounds of formula (VII) to compounds of formula (IIIb) are described by E. J. Corey and D. L. Boger Tet. Letters, (1978), 5; T. H. Chan Acc. Chem. Res., (1977), 10, 442 and B. H. Lipshutz and R. W. Hungate J. Org. Chem., (1981), 46, 1410.

Compounds of formula (IV) are produced by the methods shown in Scheme II:

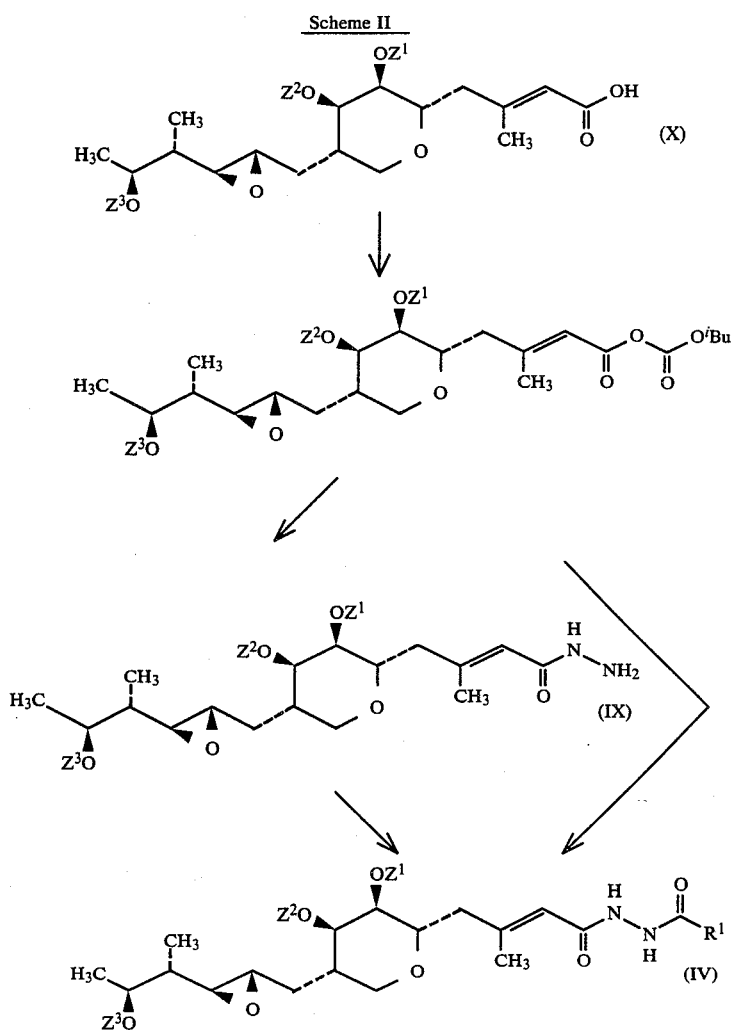

Compounds of formula (V) are generically described in European Patent Application No. 01914. Conveniently they may be produced by reacting a compound of formula (X)

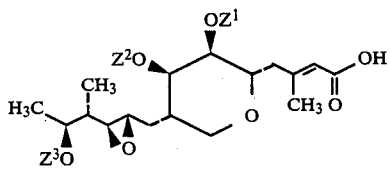

or a reactive derivative thereof
wherein $Z^1$, $Z^2$ and $Z^3$ are the same or different and each is hydrogen or a hydroxyl-protecting group, with a compound of formula (XI)

$R^1NH_2$ (XI)

wherein $R^1$ is as defined in relation to compounds of formula (I).

The reaction between a compound of formula (X) and a compound of formula (XI) is suitably effected by treating the compound of formula (X) with isobutyl chloroformate and a tertiary amine such as triethylamine and then the compound of formula (XI) together with a catalytic amount of dimethylaminopyridine.

The compound of formula (X) wherein $Z^1$, $Z^2$ and $Z^3$ are hydrogen is monic acid, and processes for its production, are described in U.K. Pat. No. 1,587,058. Derivatives thereof wherein $Z^1$, $Z^2$ and $Z^3$ are hydroxyl protecting groups may be produced by conventional methods such as those mentioned below. When this compound is produced with hydroxyl protecting groups already in place it may be used directly or even in situ in the above reaction or it may be optionally deprotected and/or isolated.

The compoundss of formula (XI) are known and either commercially available or may be produced by known methods.

Compounds of formula (VI) may be produced by reacting a compound of formula (X) or a reactive derivative thereof, with a compound of formula (XII)

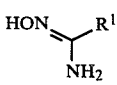

wherein R¹ is as defined in relation to compounds of formula (I).

Suitable reactive derivatives of compounds of formula (X) include mixed anhydrides; preferably the anhydride of monic acid and iso-butylchloroformate is used. Conveniently the reaction is effected in a solvent such as tetrahydrofuran in the presence of a tertiary amine such as triethylamine.

Compounds of formula (IV) and (IX) are novel and useful as intermediates in the synthesis of compounds of formula (IA).

Accordingly the present invention provides, in another aspect, a compound of formula (XIII):

(XIII)

wherein Y is hydrogen or a group $$-\overset{O}{\underset{\|}{C}}-R^1,$$

R¹ is as defined in relation to compounds of formula (I) and $Z^1$, $Z^2$ and $Z^3$ are the same or different and each is hydrogen or a hydroxyl protecting group.

Certain compounds of formula (V) are not specifically disclosed in European Patent Application No. 01914 but are particularly important as intermediates for favoured compounds of formula (I).

Accordingly the present invention provides a compound of formula (VA)

(VA)

wherein R¹ is p-nitrophenyl, m-cyanophenyl or p-methylsulphonyl phenyl.

Compounds of formula (VI) are novel and useful as intermediates in producing compounds of formula (I).

Accordingly the present invention provides a compound of formula (VI) as hereinbefore defined.

The hydroxyl groups of monic acid, and compounds of formulae (II) and (IV) may be protected at any stage of the above processes, using conventional methods.

Particularly suitable protecting groups are silyl groups since these are readily removed under mild conditions. Such groups are introduced using conventional silylating agents, including halosilanes and silazanes, of the formulae below:

| | |
|---|---|
| $L_3SiX$ | $L_3SiO-\underset{\underset{L}{\|}}{C}=NSiL_3$ |
| $L_2SiX_2$ | |

-continued

| | |
|---|---|
| $L_3SiNL_2$ | $Me_3Si-N\underset{\underline{\qquad}}{\overset{\frown}{\diagdown}}N$ |
| $L_3SiNHSiL_3$ | |
| $L_3SiNHCOL$ | |
| $L_3SiNHCONHSiL_3$ | $^tBuMe_2Si-N\underset{\underline{\qquad}}{\overset{\frown}{\diagdown}}N$ |
| $LNHCONHSiL_3$ | $^tBuMe_2Si-O-SO_2-CF_3$ | wherein X is halogen and each group L is independently selected fro hydrogen, alkyl, alkoxy, aryl or aralkyl. A preferred silyating agent is trimethylsilyl chloride. Particularly suitable protecting groups are trimethylsilyl, t-butyldimethylsilyl and t-butyldiphenylsilyl groups. Preferred protecting groups are trimethylsilyl groups because of their ease of removal.

The glycol function of monic acid and the compounds of formulae (II) and (IV) may be protected by forming a cyclic derivative using a compound of formula (XIV):

$$R^4-\underset{\underset{OR^5}{\|}}{\overset{\overset{OR^6}{\|}}{C}}-OR^7 \quad (XIV)$$

wherein R⁴ is hydrogen or $C_{1-6}$ alkyl and each of R⁵, R⁶ and R⁷ is $C_{1-6}$ alkyl. In the cyclic derivative $Z^1$ and $Z^2$ together are a moiety:

$$\underset{\diagup \diagdown}{\overset{R^4 \diagdown \diagup OR^8}{C}}$$

wherein R⁸ is $C_{1-6}$ alkyl.

Suitably R⁴ is hydrogen, methyl, ethyl, n- or iso-propyl; most suitably it is hydrogen. The groups R⁵, R⁶ and R⁷ are suitably methyl, ethyl, n- or iso-propyl, n-, iso-, sec- or t-butyl; most suitably methyl.

Similarly the hydroxyl groups of a compound of formula (I) may be protected prior to conversion to a further compound of formula (I) as described above.

In each case the protecting groups described above may be removed by mild acid hydrolysis followed by alkaline hydrolysis, for instance, as described by J. P. Clayton, K. Luk and N. H. Rogers, in 'Chemistry of Pseudomonic Acid, Part II', *J. C. S. Perkin Trans. I*, 1979, 308.

The infections against which compounds of this invention are particularly useful include venereal disease. They are also effective in the treatment of respiratory infections such as bacterial bronchitis; and bacterial meningitis, non-specific urethritis and pneumonia. In animals they may be employed for the treatment of mastitis in cattle, for swine dysentery, and for mycoplasma infections and eye infections in animals such as turkeys, chickens, pigs and cattle.

Some of the human and veterinary diseases either caused by mycoplasma species or in which they play a prominent role, and against which compounds of this invention are effective, are as follows:

| | |
|---|---|
| Avian | |
| M. gallisepticum | chronic respiratory diseases (air-sacculitis) of chickens and turkeys |
| Bovine | |
| M. bovis | mastitis, respiratory disease and arthritis of cattle |
| M. dispar | calf pneumonia |
| Porcine | |
| M. hyopneumoniae | enzootic pneumonia of pigs |
| M. hyorhinis | arthritis in pigs |
| M. hyosynoviae | |
| Human | |
| M. pneumoniae | primary atypical pneumonia |

Compounds of the present invention are particularly useful in the treatment of mycoplasmal and/or bacterial pneumonia in animals such as pigs, cattle and sheep, because they also have activity against the bacteria *Bordetella bronchiseptica, Pasteurella multocida* and *Haemophilus spp*, which are often involved in the disease.

This invention also provides a pharmaceutical or veterinary composition which comprises a compound of formula (I) (hereinafter referred to as the 'drug') together with a pharmaceutically or veterinarily acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin the drug may be made up into a cream, lotion or ointment. Cream or ointment formulations that may be used for the drug are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butters or other glyceride.

For parenteral administration, fluid unit dosage forms are prepared utilizing the drug and a sterile vehicle. The drug, depending on the vehicle and concentration used, can either be suspended or dissolved in the vehicle. In preparing solutions the drug can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lyophilized powder is then sealed in the vial. Parenteral suspensions are prepared in substantially the same manner except that the drug is suspended in the vehicle instead of being dissolved and sterilisation cannot be accomplished by filtration. The drug can be sterilised by exposure to ethylene oxide before suspending in the sterile vehicle. Advantageously, a surfactant or wetting agent is included in the composition to facilitate uniform distribution of the drug.

For topical application to the ear, the drug may be made up into a solution or suspension in a suitable liquid carrier, such as water, glycerol, diluted ethanol, propylene glycol, polyethylene glycol or fixed oils.

For topical application to the eye, the drug is formulated as a solution or suspension in a suitable, sterile aqueous or non-aqueous vehicle. Additives, for instance buffers such as sodium metabisulphite or disodium edetate; preservatives including bactericidal and fungicidal agents, such as phenylmercuric acetate or nitrate, benzalkonium chloride or chlorhexidine, and thickening agents such as hypromellose may also be included.

The dosage employed for compositions administered topically will, of course, depend on the size of the area being treated. For the ears and eyes each dose will typically be in the range from 10 to 100 mg of the drug.

Veterinary compositions for intramammary treatment of mammary disorders in animals, especially bovine mastitis, will generally contain a suspension of the drug in an oily vehicle.

The compositions may contain from 0.1% to 99% by weight, preferably from 10–60% by weight, of the drug, depending on the method of administration. Where the compositions are in unit dose form, each dosage unit will preferably contain from 50–500 mg, of the drug. The dosage as employed for adult human treatment will preferably range from 100 mg to 3 g, per day, for instance 250 mg to 2 g of the drug per day, depending on the route and frequency of administration.

Alternatively, the drug may be administered as part of the total dietary intake. In this case the amount of drug employed may be less than 1% by weight of the diet and in preferably no more than 0.5% by weight. The diet for animals may consist of normal foodstuffs to which the drug may be added or the drug may be included in a premix for admixture with the foodstuff.

A suitable method of administration of the drug to animals is to add it to the animals' drinking water. In this case a concentration of the drug in the drinking water of about 5–500 $\mu$g/ml, for example 5–200 $\mu$g/ml, is suitable.

The present invention further provides a method for treating the human, or non-human animal which method comprises administering a compound of formula (I) as hereinbefore defined, to a human or non-human in need of such therapy.

Alternatively, a pharmaceutical composition as hereinbefore described may be employed in the treatment.

In particular aspects of the treatment there are provided methods for treating bacterial and/or mycoplasmal infections of human or non-human animals, especially venereal disease, respiratory infections such as bacterial bronchitis, bacterial meningitis, non-specific urethritis and pneumonia in humans, respiratory infections, mastitis, swine dysentery and pneumonia in animals.

The following Examples illustrate the invention, but are not intended to limit the scope in any way.

The following abbreviations have been used in the Examples:
DMF: N,N-dimethylformamide
THF: Tetrahydrofuran
MgSO$_4$: Anhydrous magnesium sulphate
Celite: (Trade Mark) is a grade of diatomaceous earth

EXAMPLE 1

2-(1-Normon-2-yl)-5-phenyl-1,3,4-oxadiazole A

A mixture of benzohydrazide (2 g, 15 mmol) and triethyl orthoacetate (15 ml, excess) was heated at 150° C. for 6 h and then evaporated in vacuo. The residue was recrystallised from hexane to give 2-methyl-5-phenyl-1,3,4-oxadiazole as shiny white plates, mp 62°–63° C. (1.4 g, 58%); $\delta$H(CDCl$_3$) 7.5 and 8.0 (5H, 2m, aryl), 2.6 (3H, s, Me).

To a solution of 3R,4R-dihydroxy-5S-(2S,3S-epoxy-5S-hydroxy-4S-methyl-hexyl)tetrahydropyran-2S-yl acetone (600 mg, 2.0 mmol) in dry THF (20 ml) was added triethylamine (0.97 ml, 7.0 mmol), trimethylsilyl chloride (0.89 ml, 7.0 mmol) and a catalytic amount of 4-(N,N-dimethylamino)pyridine. After stirring at room temperature for 2 h the triethylamine hydrochloride was filtered off and the solution concentrated in vacuo. The resultant oil was taken up in the anhydrous ether, filtered, solvent removed in vacuo, then the oil taken up in dry THF ready for the next stage of the reaction.

A solution of 2-methyl-5-phenyl-1,3,4-oxadiazole (0.35 g, 2.2 mmol) and n-butyl lithium (2.2 mmol) in dry THF (5 ml) was stirred at −78° C. for 10 min. To the metalated species produced was added trimethylsilyl chloride (0.28 ml, 2.2 mmol) and this mixture stirred at −78° C. for 30 minutes, followed by a further 30 minutes at −78° C. to 0° C. The resultant solution was cooled to −78° C. and a further equivalent of butyl lithium (2.1 mmol) added. Stirring was continued for 45 minutes before adding the protected ketone, vide supra, and allowing to warm to room temperature. The mixture was quenched with ammonium chloride then extracted with ethyl acetate and dried (MgSO$_4$). Solvent removal in vacuo gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO$_4$) and solvent removal in vacuo gave the crude product which was chromatographed (20 g silicagel, 0 to 10% methanol in dichloromethane) to give the title compound as a colourless oil (0.5 g, 6%); $\gamma_{max}$3400, 1655, 1450 cm$^{-1}$; $\lambda_{max}$(EtOH) 282 nm ($\epsilon_m$14,300); $\delta_H$(CDCl$_3$) 8.0–8.1 (2H, m, o-aryl), 7.45–7.6 (3H, m, m- and p-aryl), 6.34 (1H, s, H2), 2.33 (3H, s, CH$_3$-15), 1.23 (3H, d, CH$_3$-14), 0.94 (3H, d, CH$_3$-17); $\delta_C$(CDCl$_3$) 164.0 (C1), 163.3 (C5'), 151.4 (C3), 131.5 (C''), 129.0 (C4''), 126.8 (C2'', C6''), 124.0 (C3'', C5''), 109.3 (C2), 75.2 (C5), 71.2 (C13), 70.5 (C7), 68.9 (C6), 65.6 (C16), 61.2 (C11), 55.6 (C10), 43.0 (C12), 42.8 (C4), 39.8 (C8), 31.8 (C9), 20.8 (C14), 20.2 (C15), 12.6 (C17); m/e (relative intensity) 444 (M$^+$, 1%) 200 (100) (Found: M$^+$, 444.2246, C$_{24}$H$_{32}$N$_2$O$_6$ requires 444.2260).

EXAMPLE 2

2-m-Nitrophenyl-5-(1-normon-2-yl)-1,3,4-oxadiazole A

To monic acid A (1.72 g, 5 mmol) in THF (20 ml) were added triethylamine (0.70 ml, 5 mmol) and isobutyl chloroformate (0.66 ml, 5 mmol) after 20 min a solution of m-nitrobenzohydrazide (0.91 g, 5 mmol) in methanol (100 ml) was added, and after 3 h at 20° C. the resulting solution was evaporated in vacuo and subjected to chromatography (20 g silica, 0 to 20% methanol in dichloromethane) to give N°-m-nitrobenzoylmonohydrazide A as white rhombs from either dichloromethane or ether (1.5 g, 59%); m.p. 138° C.-140° C. (dec); $\gamma_{max}$(KBr) 3450, 3250, 2900–3000, 1655, 1610 cm$^{-1}$; $\lambda_{max}$ 224 nm ($\epsilon_m$ 37,700); $\delta_H$ (dmso-d$_6$) 10.7, 9.9 (2H, 2bs, NH), 8.7 (1H, m, H2'), 8.4 (1H, d, H4'), 8.3 (1H, d, H6'), 7.8 (1H, t, H5'), 5.8 (1H, s, H2), 4.5, 4.6, 4.8 (3H, 3d, OH), 2.1 (3H, s, CH$_3$-15), 1.11 (3H, d, CH$_3$-14), 0.86 (3H, d, CH$_3$-17).

N'-m-Nitrobenzoylmonohydrazide A (0.50 g, 1 mmol) in THF/acetonitrile (1:1, 50 ml) was treated with chlorotrimethylsilane (0.42 ml, 3.3 mmol), triethylamine (0.46 ml, 3.3 mmol) and 4-N,N-dimethylaminopyridine (5 mg) for 2 h at 20° C. The mixture was then filtered and evaporated in vacuo, and the resulting residue extracted with ether. The combined ether extracts were filtered and evaporated in vacuo and the resulting residue dissolved in a mixture of acetonitrile (5 ml), pyridine (5 ml), triethylamine (0.28 ml, 2 mmol) and tetrachloromethane (0.4 ml, 4 mmol). Triphenylphosphine (0.52 g, 2 mmol) was then added and the mixture stood at 20° C. for 3 h.

The reaction mixture was poured into aqueous sodium bicarbonate, and extracted with ethyl acetate. The combined extracts were washed with brine, dried (MgSO$_4$) and evaporated in vacuo to give an oil, which was dissolved in THF (40 ml) and water (10 ml). Concentrated aqueous hydrochloric acid (12 drops) was added and after 12 min the solution neutralised with ueous sodium bicarbonate and extracted with ethyl acetate. The extracts were washed with brine, dried (MgSO$_4$) and evaporated in vacuo to leave a brown oil which was purified by chromatography on silica gel (20 g) eluting with a gradient of 4 to 10% methanol in dichloromethane to give the oxadiazole as cream rhombs after crystallisation from ether (0.19 g, 39%); m.p. 94° C.–97° C.; $\gamma_{max}$ (film) 3400, 1655, 1530, 1350 cm$^{-1}$; $\lambda_{max}$ (EtOH) 271 nm ($\epsilon_m$ 25,200); $\delta_H$(CDCl$_3$) 8.86 (1H, m, H2''), 8.39 (2H, m, H4'', 6''), 7.81 (1H, t, H5''), 6.36 (1H, s, H2), 2.36 (3H, s, CH$_3$-15), 1.22 (3H, d, CH$_3$-14), 0.93 (3H, d, CH$_3$-17), $\delta_C$(CDCl$_3$-CD$_3$OD-(CD$_3$)$_2$CO) 164.9, 161.5 (C1, C5'), 153.4 (C2), 148.9 (C3''), 132.4 (C6''), 130.7 (C5''), 126.0 (C4''), 121.7 (C2''), 125.8 (C1''), 108.8 (C2), 75.1 (C5), 70.6, 70.4 (C7, 13), 68.7 (C6), 65.7 (C16), 61.0 (C11), 55.7 (C10), 43.2 (C12), 42.6 (C4), 40.0 (C8), 31.9 (C9), 20.4 (C14), 20.3 (C15), 12.3 (C17); m/e (relative intensity) 489 (M$^+$, 3%), 344 (9), 245 (100) (Found: M$^+$, 489.2131. C$_{24}$H$_{31}$N$_3$O$_8$ requires 489.2110.)

EXAMPLE 3

2-p-Methylthiophenyl-5-(1-normon-2-yl)-1,3,4-oxadiazole A

To p-methylthiobenzoic acid (1.68 g, 10 mmol) in THF (20 ml) were added triethylamine (1.39 ml, 10 mmol) and isobutylchloroformate (1.31 ml, 10 m). After 20 min at 20° C. ether (20 ml) was added, the mixture filtered, and hydrazine hydrate (0.49 ml, 10 mmol) added to the filtrate. After 1 h at 20° C. the solution was evaporated in vacuo and the residue recrystallised from water to give p-methylthiobenzohydrazide as short colourless needles (0.45 g, 25%); m.p. 140°–142° C.; $\delta_H$(dmso-d6) 9.6 (1H, bs, NH), 7.2, 7.7 (4H, ABq, aryl), 3.8 (2H, bs, NH$_2$), 2.5 (3H, s, sMe).

To monic acid A (0.69 g, 2 mmol) in THF (15 ml) were added triethylamine (0.28 ml, 2 mmol) and isobutyl chloroformate (0.26 ml, 2 mmol). After 20 min a solution of p-methylthiobenzohydrazide (0.36 g, 2 mmol) in methanol (15 ml) was added. After 2 h at 20° C. the solution was partitioned between ethyl acetate and water. The organic layer was dried (MgSO$_4$) and evaporated in vacuo, and the residue purified by chromatography (20 g silica, 0 to 20% methanol in dichloromethane) to give N'-p-methylthiobenzoylmonohydrazide A as a white foam (0.72 g, 71%); $\gamma_{max}$(film) 3400, 3260, 1645, 1600 cm$^{-1}$; $\delta_H$(CD$_3$OD) 7.8, 7.2 (4H, ABq, aryl), 5.9 (1H, s, H2), 2.5 (3H, s, sMe), 2.2 (3H, s, CH$_3$-15), 1.2 (3H, d, CH$_3$-14), 0.9 (3H, d, CH$_3$-17).

N'-p-Methylthiobenzoylmonohydrazide A (0.50 g, 1 mmol) in THF (20 ml) was treated with chlorotrimethylsilane (0.51 ml, 4 mmol), triethylamine (0.56 ml, 4 mmol) and 4-N,N-dimethylaminopyridine 5 mg) for 2 h at 20° C. The mixture was then filtered and evaporated in vacuo, and the resulting residue extracted with ether. The combined ether extracts were filtered and evaporated in vacuo and the resulting residue dissolved in a mixture of acetonitrile (3 ml), pyridine (3 ml), triethylamine (0.28 ml, 2 mmol) and tetrachloromethane (0.39 ml, 4 mmol). Triphenylphosphine (0.52 g, 2 mmol) was then added and the mixture stood at 20° C. for 2 h.

The reaction mixture was poured into aqueous sodium bicarbonate, and extracted with ethyl acetate. The combined extracts were washed with brine, dried (MgSO$_4$) and evaporated in vacuo in give an oil, which was dissolved in THF (20 ml) and water (5 ml). Concentrated aqueous hydrochloric acid (6 drops) was added and after 12 min the solution neutralised with aqueous sodium bicarbonate and extracted with ethyl acetate. The extracts were washed with brine, dried (MgSO$_4$) and evaporated in vacuo to leave a brown oil which was purified by chromatography on silica gel (10 g) eluting with a gradient of 4 to 10% methanol in dichloromethane to give the oxadiazole as a colourless oil (0.34 g, 69%); $\gamma_{max}$(film) 3400, 1655, 1605, 1485 cm$^{-1}$; $\lambda_{max}$(EtOH) 226 nm ($\epsilon_m$ 11,900), 260 nm ($\epsilon_m$ 8,100), 315 nm ($\epsilon_m$=28,100); $\delta_H$(CDCl$_3$) 7.94 (2H, d, H2''), 7.31 (2H, d, H3''), 6.33 (1H, s, H2), 2.54 (3H, s, SMe), 2.32 (3H, s, CH$_3$-15), 1.21 (3H, d, CH$_3$-14), 0.94 (3H, d, CH$_3$-17).

EXAMPLE 4

2-p-Methylsulphonylphenyl-5-(1-normon-2-yl)-1,3,4-oxadiazole A

A mixture of 5-p-methylthiophenyl-2-(1-normon-2-yl)-1,3,4-oxadiazole A (0.15 g, 0.3 mmol), m-chloroperbenzoic acid (0.12 g×85%, 0.6 mmol), sodium bicarbonate (0.10 g, 1.2 mmol), and dichloromethane (10 ml) was stirred at 20° C. for 6 h. Direct chromatography (10 g silica, 0 to 20% methanol in dichloromethane) gave the sulphone as a white foam (30 mg, 19%); $\gamma_{max}$(film) 3400, 1645, 1150 cm$^{-1}$; $\lambda_{max}$(EtOH) 274 nm ($\epsilon_m$ 12,000), $\delta_H$(CDCl$_3$) 8.1, 8.3 (4H, ABq, aryl), 6.41 (1H, s, H2), 3.19 (3H, s, SO$_2$Me), 2.37 (3H, s, CH$_3$-15), 1.22 (3H, d, CH$_3$-14), 0.97 (3H, d, CH$_3$-17).

EXAMPLE 5

2-(1-Normon-2-yl)-5-(3-pyridyl)-1,3,4-oxadiazole A

To monic acid A (1.72 g, 5 mmol) in THF (20 ml) were added triethylamine (0.70 ml, 5 mmol) and isobutyl chloroformate (0.66 g, 5 mmol). After 20 min a solution of nicotinohydrazide 10.69 g, 5 mmol in methanol (20 ml) was added, and after 2 h at 20° C. the solution was evaporated in vacuo. Brine, aqueous sodium bicarbonate, and chloroform were added to the residue. The chloroform layer was discarded and the aqueous layer extracted with ethyl acetate. Drying (MgSO$_4$) and evaporation in vacuo of the extract then gave N'-3-nicotinoylmonohydrazide A as a white foam (0.45 g, 19%); $\delta_H$(CD$_3$OD) 9.0, 8.7, 8.3, 7.5 (4H, 4 m, pyridyl), 5.9 (1H, s, H2), 1.2 (3H, s, CH$_3$-15), 1.2 (3H, d, CH$_3$-14), 0.9 (3H, d, CH$_3$-17).

N'-3-Nicotinoylmonohydrazide A (230 mg, 0.5 mmol) in THF-acetonitrile (1:1, 10 ml) was treated with chlorotrimethylsilane (0.25 ml, 2 mmol), triethylamine (0.28 ml, 2 mmol) and 4-N,N-dimethylaminopyridine (5 mg) for 2 h at 20° C. The mixture was then filtered and evaporated in vacuo, and the resulting residue extracted with ether. The combined ether extracts were filtered and evaporated in vacuo and the resulting residue dissolved in a mixture of acetonitrile (3 ml), pyridine (3 ml), triethylamine (0.14 ml, 1 mmol) and tetrachloromethane (0.19 ml, 2 mmol). Triphenylphosphine (0.26 g, 1 mmol) was then added and the mixture stood at 20° C. for 3 h.

The reaction mixture was poured into aqueous sodium bicarbonate, and extracted with ethyl acetate. The combined extracts were washed with brine, dried (MgSO$_4$) and evaporated in vacuo to give an oil, which was dissolved in THF (20 ml) and water (5 ml). Concentrated aqueous hydrochloric acid (6 drops) was added and after 12 min the solution neutralised with aqueous sodium bicarbonate and extracted with ethyl acetate. The extracts were washed with brine, dried (MgSO$_4$) and evaporated in vacuo to leave a brown oil which was purified by chromtography on silica gel (10 g) eluting with a gradient of 4 to 15% methanol in dichloromethane to give the oxidiazole as a white foam (90 mg, 41%); $\gamma_{max}$(film) 3400, 1655, 1605, 750 cm$^{-1}$; $\lambda_{max}$(EtOH) 284 nm ($\epsilon_m$ 18,900); $\delta_H$(CDCl$_3$) 9.22 (1H, m, H2''), 8.72 (1H, m, H6''), 8.32 (1H, d, H4''), 7.49 (1H, m, H5''), 6.32 (1H, s, H2), 2.29 (3H, s, CH$_3$-15), 1.19 (3H, d, CH$_3$-14), 0.89 (3H, d, CH$_3$-17).

EXAMPLE 6

2-(1-Normon-2-yl)-5-(2-thienyl)-1,3,4-oxadiazole A

Monic acid A (3.44 g, 10 mmol) was dissolved in THF (100 ml), cooled to 0° C. and treated with triethylamine (1.5 ml, 11 mmol) and isobutyl chloroformate (1.4 ml, 11 mmol). After stirring for 20 mins thiophene-2-carboxylic hydrazide (1.42 g, 10 mmol) was added and the reaction stirred for a further 5 h. The reaction mixture was filtered, the filtrate evaporated in vacuo and the residue taken up in methanol. After filtering, the solution was evaporated in vacuo to yield N'-2-thienoyl monohydrazide A as a white foam (4.22 g, 90%); $\gamma_{max}$(film) 3400, 3250, 1640, 1535 cm$^{-1}$; $\lambda_{max}$(EtOH) 223 nm ($\epsilon_m$ 15,101); $\delta_H$(CD$_3$OD) 7.72 (1H, d, H-5″), 7.60 (1H, d, H-3″), 7.05 (1H, t, H-4″), 5.85 (1H, s, H-2), 2.15 (3H, s, CH$_3$-15), 1.15 (3H, d, CH$_3$-14), 0.9 (3H, d, CH$_3$-17).

N′-2-Thienoyl monohydrazide A (0.93 g, 2 mmol) was dissolved in THF (50 ml) and treated with trimethylsilyl chloride (1.1 ml, 8.6 mmol), triethylamine (1.2 ml, 8.6 mmol) and a few crystals of 4-dimethylaminopyridine. After 2 h the reaction was filtered, and the filtrate evaporated in vacuo. The residue was dissolved in a mixture of acetonitrile (3 ml), pyridine (3 ml), triethylamine (0.6 ml, 4 mmol) and carbon tetrachloride (0.8 ml, 8 mmol) and stirred with triphenylphosphine (1.1 g, 4 mmol) at 60° C. for 1½ h. The reaction was then evaporated in vacuo and the residue taken up in ethyl acetate, washed with aqueous sodium bicarbonate, evaporated in vacuo. The oxadiazole was deprotected using THF (75 ml), water (20 ml), and concentrated hydrochloric aicd (20 drops). After 5 mins the reaction was quenched with aqueous sodium bicarbonate and extracted with ethyl acetate. The organic layer was evaporated in vacuo and the residue purified by chromatography using silica gel (8 g) eluting with a gradient of 0 to 6% methanol in dichloromethane to yield the title compound as a pale yellow oil (217 mg, 24%); $\gamma_{max}$(film) 3400, 1655, 1590, 1535, 1510, 1490 cm$^{-1}$; $\lambda_{max}$(EtOH) 299 nm ($\epsilon_m$ 21,041); $\delta_H$(CDCl$_3$) 7.7 (1H, d, H-5″), 7.55 (1H, d, H-3″), 7.15 (1H, t, H-4″), 6.30 (1H, s, H2), 2.30 (3H, s, CH$_3$-15), 1.20 (3H, d, CH$_3$-14), 0.90 (3H, d, CH$_3$-17).

EXAMPLE 7

2-(1-Normon-2-yl)-5-(4-pyridyl)-1,3,4-oxadiazole A

Monic acid A (3.44 g, 10 mmol) was dissolved in THF (100 ml) cooled to 0° C. and treated with triethylamine (1.5 ml, 11 mmol) and isobytylchloroformate (1.4 ml, 11 mmol). After stirring for 20 mins isonicotinic acid hydrazide (1.37 g, 10 mmol) was added and the reaction stirred for 3½ h. The triethylamine hydrochloride was filtered off and the filtrate evaporated in vacuo. Ethyl acetate and brine were added and the residual solid filtered to give the N′-isonicotinoyl monohydrazide A as a white solid m.p. 134°–135° C. (1.79 g, 39%); $\gamma_{max}$(KBr) 3560, 3450, 3220, 1690, 1665, 1640, 1555 cm$^{-1}$; $\lambda_{max}$(EtOH) 219 nm ($\epsilon_H$ 14,938); $\delta_H$(CD$_3$OD) 8.65 and 7.75 (4H, ABq, pyridyl), 5.85 (1H, s, H-2), 2.15 (3H, s, CH$_3$-15), 1.15 (3H, d, CH$_3$-14), 0.90 (3H, d, CH$_3$-17).

N′-isonicotinoyl monohydrazide A (0.93 g, 2 mmol) was dissolved in a mixture of THF (50 ml) and acetonitrile (20 ml) then treated with trimethylsilylchloride (1.1 ml, 8.7 mmol), triethylamine (1.2 ml, 8.6 mmol) and a few crystals of 4-dimethylaminopyridine, for 1 h. The reaction was then filtered, and the filtrate evaporated in vacuo. The residue was dissolved in acetonitrile (5 ml), pyridine (5 ml), triethylamine (0.6 ml, 4 mmol) and carbon tetrachloride (0.8 ml, 8 mmol) and stirred with triphenylphosphine (1.1 g, 4 mmol) at 60° C. for 1 h. After evaporation the residue was taken up in ethyl acetate, washed with brine, and evaporated in vacuo. The resulting residue was deprotected using THF (40 ml), water (10 ml), concentrated hydrochloric acid (15 drops) for 5 mins and then quenched with aqueous sodium bicarbonate. The reaction mixture was extracted with ethyl acetate, dried (MgSO$_4$), and evaporated in vacuo. The residue was purified by chromatography using silica gel (10 g) elutine with a gradient of 0 to 6% methanol in dichloromethane to yield the title compound as a pale yellow foam (123.6 mg, 14%), $\gamma_{max}$(film) 3450, 1705, 1610, 1575, 1530 cm$^{-1}$; $\lambda_{max}$(EtOH) 219 nm ($\epsilon_m$ 15,817), 285 nm ($\epsilon_m$ 22,294); $\delta_H$(CD$_3$OD) 8.70 and 7.90 (4H, ABq, pyridyl), 6.35 (1H, s, H-2), 2.30 (3H, s, CH$_3$-15), 1.20 (3H, d, CH$_3$-14), 0.95 (3H, d, CH$_3$-17).

EXAMPLE 8

2-(2-Furyl)-5-(1-normon-2-yl)-1,3,4-oxadiazole A

Isobutyl mixed anhydride of monic acid A was prepared from monic acid A (3.44 g, 10 mmol), triethylamine (1.5 ml, 11 mmol) and isobutylchloroformate (1.4 ml, 11 mmol) at 0° C. for 20 mins. 2-Furoic acid hydrazide (1.26 g, 10 mmol) was added and the reaction stirred for 4 h then filtered and the filtrate evaporated in vacuo. The residue was washed with ethyl acetate and the resulting solid recrystallised from ether to yield N′-2-furoyl monohydrazide A m.p. 58°–61° C. (3.38 g, 75%); $\gamma_{max}$(KBr) 3400, 3260, 1650, 1590 cm$^{-1}$; $\lambda_{max}$(EtOH) 221 nm ($\epsilon_m$ 16,020), 250 nm ($\epsilon_m$ 15,966); $\delta_H$(CD$_3$OD) 7.70 (1H, s, H-5″), 7.20 (1H, d, H-3″), 6.60 (1H, dd, H-4″), 5.85 (1H, s, H-2), 2.20 (3H, s, CH$_3$-15), 1.20 (3H, d, CH$_3$-14), 0.95 (3H, d, CH$_3$-17).

N′-2-Furoyl monohydrazide A (0.9 g, 2 mmol) was heated at 60° C. for ½ h with acetonitrile (5 ml), pyridine (5 ml), triethylamine (0.6 ml, 4 mmol), carbon tetrachloride (0.8 ml, 8 mmol) and triphenyl phosphine (1.1 g, 4 mmol). The reaction mixture was then evaporated in vacuo and purified by chromatography twice on silica gel (10 g, 8 g) eluting with a gradient of 0 to 4% methanol in dichloromethane to yield the title compound as a pink foam (365 mg, 42%); $\gamma_{max}$(film) 3400, 1730, 1660, 1630, 1620, 1520 cm$^{-1}$; $\lambda_{max}$(EtOH) 290 nm ($\epsilon_m$ 20,851); $\delta_H$(CDCl$_3$) 7.45 (1H, s, H-5″), 7.10 (1H, d, H-3″), 6.55 (1H, m, H-4″), 6.30 (1H, s, H-2), 2.25 (3H, s, CH$_3$-15), 1.15 (3H, d, CH$_3$-14), 0.90 (3H, d, CH$_3$-17).

EXAMPLE 9

Monohydrazide A

To a solution of monic acid A (1.0 g, 3 mmol) in dry THF (20 ml) was added triethylamine (0.42 ml, 3 mmol) and then isobutyl chloroformate (0.39 ml, 3 mmol). After 10 min at 20° C. the mixture was filtered and the filtrate evaporated in vacuo. The resulting residue was dissolved in methanol (10 ml) and then hydrazine hydrate (0.5 ml, 10 mmol) was added. After 1 h at 20° C. the solution was evaporated in vacuo and the residue was purified by chromatography (20 g silica gel, 10 to 30% methanol in dichloromethane) to give the hydrazide as a colourless oil (0.35 g, 33%); $\gamma_{max}$(film) 3320, 1660, 1630 cm$^{-1}$; $\lambda_{max}$(EtOH) 222 nm ($\epsilon_m$ 12,600); $\delta_H$(CD$_3$OD) 5.69 (1H, s, H2), 2.16 (3H, s, CH$_3$-15), 1.20 (3H, d, CH$_3$-14), 0.95 (3H, d, CH$_3$-17); $\delta_C$(CD$_3$OD) 169.0 (C1), 152.6 (C3), 118.7 (C2), 76.1 (C5), 71.5 (C13), 70.6 (C7), 69.9 (C6), 66.2 (C16), 61.2 (C11), 56.7 (C10), 43.5 (C4, C12), 41.4 (C8), 32.9 (C9), 20.4 (C14), 19.0 (C15), 12.2 (C17); m/e (relative intensity) 359 (MH$^+$, 1%), 327 (9), 309 (9), 227 (21), 69 (100) (Found: MH$^+$, 359.2193, C$_{17}$H$_{31}$N$_2$O$_6$ requires 359.2187).

EXAMPLE 10

2-(4-Dimethylaminophenyl)-5-(1-normon-2-yl)-1,3,4-oxadiazole A

Monic acid A (3.44 g, 10 mmol) was dissolved in THF (100 ml) and cooled to 0° C. Triethylamine (1.5 ml, 11 mmol) and isobutylchloroformate (1.4 ml, 11 mmol) were added and stirred for 30 min. Dimethylaminobenzahydrazide (1.79 g, 10 mmol) was added and the reaction mixture stirred for 5 h. The reaction mixture was then filtered and evaporated under reduced pressure. The residue was crystallised from ether to yield p-dimethylaminobenzoylmonohydrazide A as a white solid m.p. 116°–118° C. (4.54 g, 90%); $\gamma_{max}$ (KBr) 3400 (br), 1670, 1610, 1510, 1440 cm$^{-1}$; $\lambda_{max}$ (EtOH) 221 nm ($\epsilon_m$ 23,345), 306 nm ($\epsilon_m$ 25,770); $\delta H(CD_3OD)$ 7.78 and 6.75 (4H, ABq, aryl), 5.89 (1H, s, H2), 3.04 (6H, s, N(CH$_3$)$_2$), 2.21 (3H, s, CH$_3$-15), 1.21 (3H, d, CH$_3$-14), 0.96 (3H, d, CH$_3$-17); $\delta C(CD_3OD)$ 169.14, 168.4 (C1', C1), 155.0, 154.6 (C1'', C3), 130.1, 112.1 (C2'', 3'', 5'', 6''), 119.8 (C4'), 118.4 (C2), 76.3 (C5), 71.6 (C13), 70.7 (C7), 70.0 (C6), 66.3 (C16), 61.3 (C11), 56.9 (C10), 43.7, 43.6 (C4, 12), 41.5 (C7''), 40.2 (C8), 33.0 (C9), 20.4 (C14), 19.3 (C15), 12.2 (C17); m/e (rel. int.) 505 (M$^+$, 10%), 243 (4), 165 (9), 148 (100) (found: 505.2782. C$_{26}$H$_{39}$N$_3$O$_7$ requires 505.2788).

p-Dimethylaminobenzoylmonohydrazide A (1.1 g, 2 mmol) was heated at 60° C. for 1 h with acetonitrile (5 ml), pyridine (5 ml), triethylamine (0.6 ml, 4 mmol), carbon tetrachloride (0.8 ml, 8 mmol) and triphenylphosphine (1.1 g, 4 mmol). The reaction mixture was then evaporated under reduced pressure and purified by chromatography on silicagel (13 g) eluting with a gradient of 0 to 4% methanol in dichloromethane. Rechromatographing using silicagel (10 g) and 0 to 4% methanol in dichloromethane yielded the title compound as a pale pink foam (471 mg, 48%); $\gamma_{max}$ (film) 3400 (br), 1655, 1610, 1500, 1440, 1370 cm$^{-1}$; $\lambda_{max}$ (EtOH) 334 nm ($\epsilon_m$ 40,583); $\delta H(CDCl_3)$ 7.98 and 6.74 (4H, ABq, aryl), 6.33 (1H, s, H2), 3.05 (6H, s, N(CH$_3$)$_2$), 2.31 (3H, s, CH$_3$-15), 1.21 (3H, d, CH$_3$-14), 0.92 (3H, d, CH$_3$-17); $\delta C(CDCl_3)$ 164.1 (C5'), 163.1 (C1), 152.5 (C1''), 150.3 (C3), 128.2, 111.8 (C2'', 3'', 5'', 6''), 111.0 (C4''), 109.4 (C2), 75.3 (C5), 71.0 (C13), 70.5 (C7), 69.0 (C6), 65.6 (C16), 61.2 (C11), 55.7 (C10), 43.0, 42.8 (C4, 12), 40.0 (C7''), 39.9 (C8), 32.0 (C9), 20.8 (C14), 20.1 (C15), 12.5 (C17); m/e (rel. int.) 487 (M$^+$, 25%), 272 (11), 243 (100) (Found: 487.2680. C$_{26}$H$_{37}$N$_3$O$_6$ requires 487.2682).

EXAMPLE 11

2-(m-Cyanophenyl)-5-(1-normon-2-yl)-1,3,4-oxadiazole A

To monic acid A (1.03 g, 3 mmol) and triethylamine (0.42 ml, 3 mmol) in dry THF (20 ml) at 0° C. was added isobutyl chloroformate (0.39 ml, 3 mmol). After 5 min at 0° C., a solution of m-cyanobenzohydrazide (0.48 g, 3 mmol) in methanol (20 ml) was added. The resulting solution was stirred at 0° C. for 3 h and then partitioned between brine and ethyl acetate. The organic fraction was dried (MgSO$_4$) and evaporated under reduced pressure to give a solid, which was crystallised from dichloromethane to yield N'-(m-cyanobenzoyl)monohydrazide A as chunky white crystals (1.21 g, 83%); $\gamma_{max}$ (KBr) 3300, 2230, 1645 cm$^{-1}$; $\delta$ (CD$_3$OD) 7.5–8.2 (m, 4H, aryl), 5.9 (1H, s H2), 2.2 (3H, s, CH$_3$-15), 1.2 (3H, d, CH$_3$-14), 0.9 (3H, d, CH$_3$-17).

To a solution of N'-(m-cyanobenzoyl)monohydrazide A (0.49 g, 1 mmol) in THF-acetonitrile (1:1, 20 ml) were added triethylamine (0.56 ml, 4 mmol) and chlorotrimethylsilane (0.51 ml, 4 mmol). After 3 h at room temperature the mixture was filtered and the filtrate evaporated under reduced pressure. To the resulting residue were added acetonitrile (3 ml), pyridine (3 ml), triethylamine (0.28 ml, 2 mmol), tetrachloromethane (0.38 ml, 4 mmol), and triphenylphosphine (0.52 g, 2 mmol). After 2 h at room temperature ethyl acetate and brine were added. The organic layer was dried (MgSO$_4$) and evaporated under reduced pressure. To the resulting residue was added THF-water (4:1, 50 ml) containing concentrated hydrochloric acid (15 drops). After 5 min at room temperature, excess aqueous sodium hydrogen carbonate was added, and the resulting mixture extracted with ethyl acetate, which was dried (MgSO$_4$) and evaporated under reduced pressure to give an oil. Purification of the oil by chromatography (silicagel, 0 to 10% methanol in dichloromethane) then gave the oxadiazole as a white foam (0.090 g, 20%); $\gamma_{max}$ (film) 3400, 2930, 2230, 1655, 755 cm$^{-1}$; $\lambda_{max}$ (EtOH) 283 nm ($\epsilon_m$ 15,800); $\delta_H$(CDCl$_3$) 8.30 (2H, m, H2'', H6''), 7.81 (1H, d, H4''), 7.64 (1H, t, H5''), 6.37 (1H, s, H2), 2.38 (3H, s, CH$_3$-15), 1.22 (3H, d, CH$_3$-14), 0.96 (3H, d, CH$_3$-17); $\delta_C$(CDCl$_3$) 164.6, 161.4 (C1, C5'), 152.9 (C3), 134.6 (C6''), 130.1, 130.2, 130.7 (C2'', C4'', C6''), 125.4 (C1''), 117.6 (CN), 113.7 (C3''), 108.8 (C2), 75.2 (C4), 71.1 (C7), 70.5 (C13), 68.9 (C6), 65.6 (C16), 61.1 (C11), 55.6 (C10), 43.0 (C12), 42.8 (C4), 39.8 (C8), 31.8 (C9), 20.8 (C14), 20.4 (C15), 12.6 (C17); m/e (ammonia chemical ionisation, rel. int.) 470 (MH$^+$, 100%), 452 (21), 227 (17).

EXAMPLE 12

1-(p-Nitrobenzyl)-5-(1-normon-2-yl)tetrazole A

To a solution of monic acid A (1.03 g, 3 mmol) in dry THF (45 ml) at $-10°$ C. were added triethylamine (0.46 ml, 3.3 mmol) and isobutyl chloroformate (0.43 ml, 3.3 mmol). After 30 min, p-nitrobenzylamine (0.46 g, 3 mmol) was added and the reaction stirred overnight at room temperature then poured into brine and extracted with ethyl acetate. The extracts were washed with aqueous sodium hydrogen carbonate, brine, then dried (MgSO$_4$) and evaporated under reduced pressure. The resulting residue was recrystallised from dichloromethane to yield p-nitrobenzyl monamide A as pale pink crystals (943 mg, 66%), m.p. 147°–148° C.; $\gamma_{max}$ (KBr) 3440, 1660, 1630, 1600, 1520 cm$^{-1}$; $\lambda_{max}$ (EtOH) 220 nm ($\epsilon_m$ 21,099); $\delta_H$(CD$_3$OD) 8.19 and 7.52 (4H, ABq, H2'', 3'', 5'', 6''), 5.84 (1H, s, H2), 4.50 (2H, s, CH$_2$-1'), 2.16 (3H, s, CH$_3$-15), 1.20 (3H, d, CH$_3$-14), 0.94 (3H, d, CH$_3$-17); $\delta_C$(CD$_3$OD) 169.7 (C1), 153.4 (C3), 148.6 (C1''), 143.4 (C4''), 129.4 (C3'', 5''), 124.6 (C2'', 6''), 120.8 (C2), 76.4 (C5), 71.7 (C13), 70.9 (C7), 70.2 (C6), 66.4 (C16), 61.5 (C11), 57.0 (C10), 43.8 (C12), 43.3 (C4), 41.7 (C8), 33.1 (C9), 20.4 (C14), 19.1 (C15), 12.3 (C17) (Found: C, 60.21; H, 6.91; N, 5.89. C$_{24}$H$_{34}$N$_2$O$_8$ requires C, 60.25; H, 7.11; N, 5.86%).

p-Nitrobenzyl monamide A (0.96 g, 2 mmol) in dry THF (20 ml) was treated with triethylamine (0.80 ml, 6 mmol) and trimethylchlorosilane (0.80 ml, 6 mmol) for 16 h at 20° C. The mixture was then filtered and the filtrate evaporated under reduced pressure. The resulting residue was taken up in dichloromethane (20 ml) and then triethylamine (0.40 ml, 3 mmol) and phosgene (2 ml×1.15M solution in toluene, 2.3 mmol) were added. After 30 min at 20° C., tetramethylguanidinium azide (0.8g, 5 mmol) was added and the mixture then stood for 16 h at 20° C. The mixture was partitioned between aqueous sodium hydrogen carbonate and ethyl acetate and the organic layer dried (MgSO$_4$) and evaporated under reduced pressure. The resulting residue was taken up in water (20 ml) and dioxan (80 ml) and concentrated hydrochloric acid (25 drops) was added.

After 12 min at 20° C. the solution was partitioned between aqueous sodium hydrogen carbonate and ethyl acetate. The organic layer was dried (MgSO$_4$) and evaporated under reduced pressure, and the resulting residue purified by chromatography (20 g silicagel, 0 to 10% dichloromethane in methanol) to give the tetrazole as a yellow foam (60 mg, 6%); $\gamma_{max}$ (film) 3420, 1655, 1610, 1425, 1350 cm$^{-1}$; $\lambda_{max}$ (EtOH) 243 nm ($\epsilon_m$ 14,500); $\delta_H$(CDCl$_3$) 8.24 (2H, d, H3″, H5″), 7.41 (2H, d, H2″, H6″), 6.03 (1H, s, H2), 5.60 (2H, s H1′), 2.21 (3H, s CH$_3$-15), 1.21 (3H, d, CH$_3$-14), 0.96 (3H, d, CH$_3$-17); $\delta_C$(CDCl$_3$) 153.2 (C1), 152.0 (C3), 148.3 (C1″), 140.6 (C4″), 128.7 (C3″, C5″), 124.3 (C2″, C6″), 106.3 (C2), 75.0 (C5), 71.3 (C13), 70.6 (C7), 68.9 (C6), 65.4 (C16), 61.0 (C11), 55.6 (C10), 49.8 (C1′), 42.8 (C12), 42.6 (C4), 40.1 (C8), 31.8 (C9), 20.9 (C14), 20.2 (C15), 12.7 (C17); m/e (relative intensity) 503 (M+, 1%) 259 (12), 106 (100) (Found: M+ 503.2323, C$_{24}$H$_{33}$N$_5$O$_7$ requires 503.2351).

EXAMPLE 13

1-(8-Methoxycarbonyloctyl)-5-(1-normon-2-yl)-1H-tetrazole A

Isobutyl chloroformate (0.4 ml) was added to a solution of monic acid A (1.03 g) and triethylamine (0.46 ml) in THF (30 ml) at 0° C. After stirring at room temperature for 1 h methyl 9-aminooctanoate hydrobromide (1.2 g) was added followed by triethylamine (0.8 ml) and 4-dimethylaminopyridine (few crystals). The reaction was stirred at room temperature overnight then poured into saturated aqueous ammonium chloride solution and extracted with ethyl acetate. The extracts were dried (MgSO$_4$) and evaporated under reduced pressure to an oil which was chromatographed on silica (5 g) eluting with 0 to 6% methanol in dichloromethane. Pure fractions were combined to yield 8-methoxycarbonyloctyl monamide A (0.61 g, 40%); $\gamma_{max}$ (CHCl$_3$) 3440 (broad), 1725, 1660 and 1630 cm$^{-1}$; $\delta_H$(CDCl$_3$) 0.91 (3H, d, CH$_3$-17), 1.20 (3H, d, CH$_3$-14), 2.11 (3H, s, CH$_3$-15), 3.62 (3H, s, OCH$_3$), 5.62 (1H, s, H-2), 6.14 (1H, t, NH).

The amide (513 mg) in THF (30 ml) was treated with triethylamine (0.7 ml) followed by trimethylsilyl chloride (0.6 ml) and 4-dimethylaminopyridine (catalytic amount). After 1 h the solution was filtered and the filtrate evaporated under reduced pressure to an oil which was redissolved in THF, filtered and re-evaporated to an oil. The protected amide in THF (25 ml) was cooled to −20° C. and treated with triethylamine (0.153 ml) and phosgene in toluene (1.1M, 1 ml). The reaction was stirred at room temperature for 2 h then treated with tetramethylguanidinium azide (395 mg, 2.5 eq.) and stirred for 3 h at room temperature. The reaction was poured into saturated aqueous ammonium chloride solution and the product extracted with ethyl acetate. The combined extracts were dried (MgSO$_4$) and evaporated under reduced pressure to an oil which was taken up in THF-water (4:1, 20 ml) and treated with 10M hydrochloric acid (10 drops). After 7 min excess saturated aqueous sodium hydrogen carbonate was added and the product extracted with ethyl acetate. The combined extracts were washed with brine, dried (MgSO$_4$) and evaporated under reduced pressure to an oil which was chromatographed on silica (7.5 g) eluting with 0 to 6% methanol in dichloromethane. Fractions containing pure product were combined and evaporated to yield (130 mg, 24%); m.p. 80°–80.5° C.; $\gamma_{max}$ (CHCl$_3$) 3430 (broad), 1736, 1708 and 1646 cm$^{-1}$; $\lambda_{max}$ (EtOH) 236 nm ($\epsilon_m$ 13,168); $\delta_H$ (CDCl$_3$) 0.92 (3H, d, CH$_3$-17), 1.22 (3H, d, CH$_3$-14), 1.32 (8H, m), 1.60 (2H, m), 1.87 (2H, m) [(CH$_2$)$_6$], 2.25 (3H, s, CH$_3$-15), 2.30 (2H, t, CH$_2$CO$_2$CO$_2$Me), 3.67 (3H, s, OCH$_3$), 4.27 (2H, t, CH$_2$-tet), 6.10 (1H, s, H-2); $\delta_C$ (CDCl$_3$) 174.4 (Cl′), 152.0 and 151.7 (Cl, 3), 106.7 (C2), 75.1 (C5), 71.2 (C13), 70.5 (C7), 68.9 (C6), 65.5 (C5), 61.2 (C11), 55.7 (C10), 51.5 (OCH$_3$) 47.1 (C9′), 42.8 (C4,12), 39.9 (C8′), 34.1 (C2′), 31.8 (C9), 29.5, 29.0, 29.0 28.7, 26.3 (C4′, 5′, 6′, 7′, 8′), 24.9 (C3′), 20.8 (C14), 20.1 (C15), 12.6 (C17); m/e (relative intensity) 538 (M+, 4%) 507 (7), 393 (15), 294 (100) (Found: 538.3367. C$_{27}$H$_{46}$N$_4$O$_7$ requires 538.3366).

EXAMPLE 14

Sodium 1-(8-carboxylatooctyl)-5-(1-normon-2-yl)-1H-tetrazole A

A solution of 1-(8-methoxycarbonyloctyl)-5-(1-normon-2-yl)-1H-tetrazole A (106 mg) in trimethyl orthoformate (25 ml) was treated with p-toluenesulphonic acid (few crystals) and stirred for 0.75 h. The solution was evaporated and 1M sodium hydroxide (2.5 ml) in water (7.5 ml) immediately added, followed by THF (10 ml). The reaction was stirred at room temperature for 2 h and the pH adjusted to 2. After 10 min the pH was adjusted to 9 and the solution left for 0.75 h. The pH was then adjusted to 4 and the product extracted into ethyl acetate (3×20 ml). The extracts were dried (MgSO$_4$) and evaporated under reduced pressure to dryness and the residue chromatographed on silica 1.5 g) eluting with 0 to 10% methanol in dichloromethane. Pure fractions were combined and evaporated under reduced pressure to yield free acid (68 mg) which was taken up in methanol (3 ml) and treated with sodium hydrogen carbonate (11 mg) in water (3 ml). The solution was evaporated to dryness to yield the title compound (71 mg, 66%); $\lambda_{max}$ (EtOH) 226 nm ($\epsilon_m$ 19,669); $\delta_H$(D$_2$O) 0.95 (3H, d, CH$_3$-17), 1.18 (3H, d, CH$_3$-14), 1.25 (8H, m, (CH$_2$)$_4$), 2.05 (3H, s, CH$_3$-15), 2.12 (2H, t, CH$_2$CO$_2$−), 4.38 (2H, t, CH$_2$-tet), 6.25 (1H, s, H-2); $\delta_C$(D$_2$O) 184.4 (C1′), 152.9 and 152.8 (C1, 3), 107.6 (C2), 75.4 (C5), 70.5 (C13) 70.4 (C7), 69.4 (C6), 65.9 (C16), 62.1 (C11) 57.5 (C10), 48.2 (C9′), 42.7 (C12), 42.0 (C4), 39.9 (C8), 38.5 (C2′), 31.9 (C9), 29.6, 29.5, 29.2, 28.8, 26.7, 26.3 (C3′–8′), 19.7 (C14), 19.6 (C15), 11.9 (C17).

EXAMPLE 15

5-(1-Normon-2-yl)-3-phenyl-1,2,4-oxadiazole A

To a solution of 3R,4R-dihydroxy-5S-(2S, 3S-epoxy-5S-hydroxy-4S-methylhexyl)tetrahydropyran-2S-yl acetone (604 mg, 2.00 mmol) in dry tHF (20 ml) was added triethylamine (1.20 ml, 7.90 mmol), trimethylsilyl chloride (1.00 ml, 7.90 mmol) and a catalytic amount of 4-(N,N-dimethylamino)-pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

A solution of 5-methyl-3-phenyl-1,2,4-oxadiazole (2.2 mmol) and butyl lithium (2.20 mmol) in dry THF at −78° C. was stirred for 10–15 minutes. To the metalated species produced was added trimethylsilyl chloride (0.28 ml, 2.20 mmol) and this mixture stirred at −78° C. for 30 minutes, follwed by a further 15 minutes at 0° C. The resultant solution was cooled to −78° C. and a further equivalent of butyl lithium (2.05 mmol) was added. Stirring was continued for 30 minutes before adding the protected ketone, vide supra, and allowing to warm to room temperature. The mixture was quenched with aqueous ammonium chloride then extracted with ethyl acetate and dried (MgSO$_4$). Solvent removal under reduced pressure gave an oil which was taken up in THF/water (100 ml, 4:1) and treated with acid (10 drops, concentrated hydrochloric acid) for 5 min. After this time the mixture was quenched with aqueous sodium hydrogen carbonate and extracted with ethyl acetate. Drying (MgSO$_4$) and solvent removal under reduced pressure gave the crude product which was chromatographed on silica (10 g, 0 to 5% MeOH/CH$_2$Cl$_2$ as eluant) to give the title compound (264 mg, 0.59 mmol, 30%); m.p. 119°–120° C.; $\gamma_{max}$ (film) 3600–3200, 2970, 2920, 1655, 1555, 1535, 1445, 1365, 1110, 1050, 910, 730, 695 cm$^{31\ 1}$; $\lambda_{max}$ (EtOH) 242 nm ($\epsilon_m$ 31,800); $\delta_H$(CD$_3$OD) 0.93 (3H, d, J=7 Hz, CH$_3$-17), 1.20 (3H, d J=7 Hz, CH$_3$-14), 1.40 (1H, m, CH-12), 1.71 (2H, m, CH$_2$-9), 1.97 (1H, m, CH-8), 2.41 (4H, s+m, CH$_3$-15+CH-4), 2.72 (1H, dd, J=2, 8 Hz, CH-11), 2.81 (2H, m, CH-10+CH'-4), 3.42 (1H, dd, J=9, 3 Hz), 3.61 (1H, d, J=12 Hz), 3.80–4.00 (4H, m), 6.41 (1H, s, CH-2), 7.52 (3H, m, C$_6$H$_5$), 8.07 (2H, m, C$_6$H$_5$); $\delta_C$(CD$_3$OD) 12.2 (C17), 20.4 (C14+C15), 32.8 (C9), 41.4 (C8), 43.5, 44.0 (C4, 12), 56.7 (C10), 61.2 (C11), 66.3 (C16), 69.8 (C6), 70.6 (C7), 71.4 (C13), 76.1 (C5), 110.6 (C2), 128.2, 129.7, 132.0 (Ph), 157.1 (C3), 169.1 (C1), 176.3 (C4'); m/e (rel. int.) 444 (M$^+$, 3%) 299 (12), 227 (28), 200 (100), 111 (28), 69 (44), 55 (34), 43 (42), 41 (33) (Found: 444.2230. C$_{24}$H$_{32}$N$_2$O$_6$ required 444.2260) and 5-(1-Norisomon-2-yl)-3-phenyl-1,2,4-oxidazole (69.7 mg, 0.16 mmol, 8%); $\gamma_{max}$ (film) 3600–3200, 2970, 2920, 1650, 1555, 1530, 1445, 1350, 1110, 1050, 730, 695 cm$^{-1}$; $\lambda_{max}$ (EtOH) 243 nm ($\epsilon_m$ 24,770); $\delta_H$(CD$_3$OD) 0.90 (3H, d, J=7 Hz, CH$_3$-17), 1.18 (3H, d, J=7 Hz, CH$_3$-14), 1.36 (1H, m, CH-12), 1.5–1.8 (2H, m, CH$_2$-9), 1.98 (1H, m, CH-8), 2.15 (3H, s, CH$_3$-15), 2.63 (1H, dd, J=8, 2 Hz, CH-11), 2.78 (1H, dt, J=2, 5 Hz, CH-10), 3.13 (1H, dd, J=12, 3 Hz, CH-4), 3.55 (2H, m), 3.7–4.0 (4H, m), 6.42 (1H, s, CH-2), 7.53 (3H, m, C$_6$H$_5$), 8.05 (2H, m, C$_6$H$_5$); $\delta_C$(CD$_3$OD) 12.2 (C17), 20.3 (C14), 26.0 (C15), 33.0 (C9), 37.0 (C8), 41.0 (C4), 43.6 (C12), 56.8 (C10), 61.3 (C11), 66.3 (C16), 70.7 (C6+C7), 71.6 (C13), 77.2 (C5), 110.7 (C2), 128.3, 129.9, 132.2 (C$_6$H$_5$), 158.1 (C3), 169.2 (C1), 176.4 (C4'); m/e (rel. int.) 444 (M$^+$, 4%) 229 (54), 200 (100), 111 (74), 82 (50), 69 (58), 55 (65), 43 (74), 41 (68) Found: 444.2272. C$_{24}$H$_{32}$N$_2$O$_6$ requires 444.2260).

EXAMPLE 16

5-(1-Normon-2-yl)-3-(4-nitrophenyl)-1,2,4-oxadiazole

To a solution of monic acid (1.70 g, 5.0 mmol) and triethylamine (0.70 ml, 5.0 mmol) in dry THF (25 ml) at 0° C. was added iso-butylchloroformate (0.65 ml, 5.0 mmol). The reaction mixture was stirred at 20° C. for 30 minutes then p-nitrophenylamidoxime (1.09 g, 6.00 mmol) added and the reaction stirred at 0° C. to room temperature for 66 h. The mixture was poured into water and extracted with ethyl acetate (2×50 ml), the organic layer was dried (MgSO$_4$) and solvent removal under reduced pressure gave an oil which was purified by column chromatography (0 to 10% MeOH/CH$_2$Cl$_2$, silica) to give 4-nitrophenylamide O-monoyloxime A (872 mg, 1.72 mmol, 34%); m.p. 172°–3° C. (MeOH); $\gamma_{max}$ (KBr) 3600–3200, 2960, 2910, 1710,, 1650, 1520, 1345, 1110, 1050, 925, 860 cm$^{-1}$; $\lambda_{max}$ (EtOH) 227 nm ($\epsilon_m$ 17,320); $\delta_H$(CD$_3$OD) 0.95 (3H, d, J=7 Hz, CH$_3$-17), 1.20 (3H, d, J=7 Hz, CH$_3$-14), 2.20 (3H, s, CH$_3$-15), 5.90 (1H, s, CH-2), 8.10 (4H, ABq, C$_6$H$_4$). 4-Nitrophenylamide O-monoyloxime A (255 mg, 0.5 mmol) was heated at 150° C. in diglyme (2.5 ml) for 1 h. The cooled solution was taken up in ethyl acetate, washed with water and dried (MgSO4). Solvent removal under reduced pressure gave the crude material (236 mg) which was purified by column chromatography (0 to 5% MeOH/CH$_2$Cl$_2$ on 4 g silica) to yield the title compound (45 mg, 0.09 mmol, 18.5%); $\gamma_{max}$ (film) 3600–3200, 2970, 2930, 1650, 1560, 1530, 1415, 1350, 1105, 1050, 730 cm$^{-1}$; $\lambda_{max\ (EtOH)}$ 265 nm ($\epsilon_m$ 26,500); $\delta_H$(CD$_3$OD) 0.93 (3H, d, J=7 Hz, CH$_3$-17), 1.20 (3H, d, J=7 Hz, CH$_3$-14), 1.40 (1H, m, CH-12), 1.71 (2H, m, CH$_2$-9), 1.98 (1H, m, CH-8), 2.43 (4H, s+m, CH$_3$-15+CH-4), 2.65-2.90 (3H, m, CH-10, 11, CH'-4), 3.4–4.0 (6H, m), 6.46 (1H, s, CH-2), 8.34 (4H, q, C$_6$H$_4$); $\delta_C$(CD$_3$OD) 12.3 (C17), 20.4, 20.5 (C14, 15), 33.1 (C9), 41.7 (C8), 43.7, 44.2 (C4, 12), 56.9 (C10), 61.4 (C11), 66.5 (C16), 70.1 (C6), 70.8 (C7), 71.7 (C13), 76.4 (C5), 110.5 (C2), 124.5 (C1''), 125.1 (C2'', 6''), 129.5 (C3'', 5''), 134.4 (C4''), 158.5 (C3), 168.0 (C1), 177.3 (C4').

EXAMPLE 17

3-(1-Normon-2-yl)-5-phenyl-1,2,4-oxadiazole

To a solution of 3R,4R-dihydroxy-5S-(2S,3S-epoxy-5S-hydroxy-4S-methyl-hexyl)tetrahydropyran-2S-yl acetone (302 mg, 1.00 mmol) in dry THF (20 ml) was added triethylamine (1.20 ml, 3.90 mmol), trimethysilyl chloride (1.00 ml, 3.90 mmol) and a catalytic amount of 4-(N,N-dimethylamino)-pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a suspension of sodium hydride (48 mg, 50% in oil, washed, 1.00 mmol) in dry tetrahydrofuran (THF, 10 ml) at 0° C. was added 3-diethylphosphonomethyl-5-phenyl-1,2,4-oxadiazole (296 mg, 1.00 mmol) in THF (5 ml). The cooling bath was removed and the mixture stirred at room temperature until hydrogen evolution had ceased and the solution was homogeneous (ca 1 h). The solution was cooled (0° C.), the protected ketone added, stirred for 30 minutes at 0° C. and at then ambient temperature for 1 h. The mixture was quenched with aqueous ammonium chloride then extracted with ethyl acetate and dried (MgSO$_4$). Solvent removal under reduced prssure gave an oil which was taken up in THF/water (100 ml, 4:1) and treated with acid (10 drops, concentrated hydrochloric acid) for 5 min. After this time the mixture was quenched with aqueous sodium hydrogen carbonate and extracted with ethyl acetate. Drying (MgSO$_4$) and solvent removal under reduced pressure gave the crude product which was chromatographed (0 to 5% MeOH/CH$_2$Cl$_2$, 5 g silica) to give the title compound (98 mg, 0.22 mmol, 22%); $\gamma_{max\ (film)}$ 3600–3200, 2970, 2920, 1660, 1610, 1550, 1500, 1450, 1110, 1050, 910, 730, 690 cm$^{-1}$; $\lambda_{max}$ (EtOH) 244 nm ($\epsilon_m$ 27,270); $\delta_H$(CDCl$_3$) 0.95 (3H, d, J=7 Hz, CH$_3$-14), 2.30 (3H, s, CH$_3$-15), 6.30 (1H, s, C-2), 7.50 (3H, m, C$_6$H$_5$), 8.10 (2H, m, C$_6$H$_5$) and 3-(1-Norisomon-2-yl)-5-phenyl-1,2,4-oxadiazole (31 mg, 0.07 mmol, 7%); $\gamma_{max}$ (film) 3600–3200, 2980, 1660, 1610, 1560, 1450, 1380, 1240, 1030, 960, 730, 695 cm$^{-1}$; $\lambda_{max}$ (EtOH) 243 nm ($\epsilon_m$ 16,120); $\delta_H$(CDCl$_3$) 0.95 (3H, d, J=7 Hz, CH$_3$-17), 1.25 (3H, d, J=7 Hz, CH$_3$-14), 2.10 (3H, s, CH$_3$15), 6.35 (1H, s, CH-2), 7.50 (3H, m, C$_6$H$_5$), 8.10 (2H, m, C$_6$H$_5$).

BIOLOGICAL DATA

(a) Mycoplasma

The activity of the normonyl derivatives of the Examples against various mycoplasmal organisms was assayed in vitro in Friis broth solidified with 0.9% agarose and inoculated with 10$^3$ to 10$^5$ C.F.U. The minimum inhibitory concentrations (MIC's) were determined after incubation for 6 days at 37° C. and are shown in Table 1.

(b) Veterinary Bacteria

The activity of the normonyl derivatives of the Examples against various veterinarily important bacteria, was assayed in vitro using two-fold serial dilutions in Diagnostic Sensitivity Test Agar inoculated with 10$^4$ organisms. The MIC's were determined after incubation for 18 hours at 37° C. and are shown in Table 2.

(c) Human Bacteria

The activity of the normonyl derivatives of the Examples against various bacteria which are important in diseases of humans, was assayed in vitro using serial dilutions in nurient agar with 5% chocolated horse blood. The MIC's were determined after incubation for 18 hours at 37° C. and are shown in Table 3.

In the following Tables the following abbreviations are used:
NT—not tested.
NG—no growth.
C—contaminated.

TABLE 1

MIC's (μg/ml) against Mycoplasma

| Organism | Compound of Example No. | | | | |
|---|---|---|---|---|---|
| | 1 | 2 | 3 | 4 | 5 |
| M. hyopneumoniae NB12 | 2.5 | 0.05 | 1.0 | 0.25 | 2.5 |
| M. hyopneumoniae JF 435 | 5.0 | 0.05 | 2.5 | 0.25 | 2.5 |
| M. hyopneumoniae HK (2) | 5.0 | 0.05 | 1.0 | 0.25 | 2.5 |
| M. hyopneumoniae Str. 11 | 2.5 | 0.025 | 1.0 | 0.25 | 1.0 |
| M. hyopneumoniae J2206/183$^b$ | 5.0 | 0.025 | 1.0 | 0.5 | 2.5 |
| M. hyopneumoniae MS 16 | 2.5 | 0.025 | 0.5 | 0.1 | 1.0 |
| M. hyopneumoniae PW/C/210 | 2.5 | NG | 0.5 | 0.1 | 1.0 |
| M. hyopneumoniae LABER | 2.5 | 0.025 | 1.0 | 0.25 | 1.0 |
| M. hyopneumoniae UCD 1 | 5.0 | 0.025 | 1.0 | 0.25 | 2.5 |
| M. hyopneumoniae TAM 6N | 5.0 | 0.05 | 2.5 | 0.5 | 2.5 |
| M. hyopneumoniae ATCC 25095 | 2.5 | 0.025 | 1.0 | 0.25 | 1.0 |
| M. hyopneumoniae NCTC 101101 | 5.0 | 0.05 | 1.0 | 0.5 | 2.5 |
| M. hyorhinis ATCC 23234 | 2.5 | 0.025 | 0.5 | 0.1 | 1.0 |
| M. hyorhinis ATCC 25021 | 1.0 | 0.025 | 0.5 | 0.1 | 1.0 |
| M. hyosynoviae ATCC 25591 | 1.0 | 0.5 | 2.5 | 1.0 | 1.0 |
| M. bovis NCTC 10131 | 0.05 | 0.025 | 0.1 | 0.05 | 0.025 |
| M. bovigenitalium ATCC 14173 | 0.1 | 0.025 | 0.5 | 0.25 | 0.25 |
| M. dispar NCTC 10125 | 0.5 | <0.01 | 0.25 | 0.25 | 0.5 |
| M. gallisepticum S6 | >10 | >10 | >10 | >10 | >10 |
| M. pneumoniae ATCC 15492 | >10 | 2.5 | >10 | >10 | >10 |

| Organism | Compound of Example No. | | | | |
|---|---|---|---|---|---|
| | 6 | 7 | 8 | 9 | 10 |
| M. hyopneumoniae NB12 | NG | NG | NG | 10 | NG |
| M. hyopneumoniae JF 435 | 5.0 | 2.5 | 10 | 10 | 1.0 |
| M. hyopneumoniae HK (2) | 5.0 | 2.5 | 10 | 10 | 5.0 |
| M. hyopneumoniae Str. 11 | 2.5 | 0.5 | 5 | 5.0 | 1.0 |
| M. hyopneumoniae J2206/183$^b$ | 5.0 | 2.5 | 10 | 10 | 5.0 |
| M. hyopneumoniae MS 16 | 2.5 | NG | NG | 5.0 | NG |
| M. hyopneumoniae PW/C/210 | NG | NG | NG | 5.0 | NG |
| M. hyopneumoniae LABER | 2.5 | NG | NG | 5.0 | NG |
| M. hyopneumoniae UCD 1 | 5.0 | 1.0 | 5 | 10 | 2.5 |
| M. hyopneumoniae TAM 6N | 5.0 | 2.5 | 10 | 10 | 5.0 |
| M. hyopneumoniae ATCC 25095 | 2.5 | NG | NG | 5.0 | NG |
| M. hyopneumoniae NCTC 101101 | 5.0 | 2.5 | 10 | 10 | 5.0 |
| M. hyorhinis ATCC 23234 | 2.5 | 0.5 | 2.5 | >10 | 1.0 |
| M. hyorhinis ATCC 25021 | 1.0 | 0.5 | 2.5 | 10 | 1.0 |
| M. hyosynoviae ATCC 25591 | 2.5 | 0.5 | 2.5 | 10 | 2.5 |
| M. bovis NCTC 10131 | 0.05 | 0.025 | 0.1 | 0.5 | 0.25 |
| M. bovigenitalium ATCC 14173 | 0.25 | 0.25 | 0.5 | 0.5 | 1.0 |
| M. dispar NCTC 10125 | 1.0 | 0.25 | 1.0 | 2.5 | 0.5 |
| M. gallisepticum S6 | >10 | >10 | >10 | >10 | >10 |
| M. pneumoniae ATCC 15492 | >10 | >10 | >10 | >10 | 10 |

| Organism | Compound of Example No. | | | | |
|---|---|---|---|---|---|
| | 11 | 12 | 13 | 14 | 15* |
| M. hyopneumoniae NB12 | 0.25 | 5.0 | >10 | >10 | 10 |
| M. hyopneumoniae JF 435 | 0.25 | 5.0 | >10 | >10 | 10 |
| M. hyopneumoniae HK (2) | 0.25 | 5.0 | >10 | >10 | 10 |
| M. hyopneumoniae Str. 11 | 0.25 | 2.5 | >10 | >10 | 5.0 |
| M. hyopneumoniae J2206/183$^b$ | 0.25 | 5.0 | >10 | >10 | 10 |
| M. hyopneumoniae MS 16 | 0.1 | 2.5 | >10 | >10 | 5.0 |
| M. hyopneumoniae PW/C/210 | 0.1 | 2.5 | >10 | NG | 5.0 |
| M. hyopneumoniae LABER | 0.25 | 2.5 | >10 | >10 | 5.0 |

TABLE 1-continued

MIC's (μg/ml) against Mycoplasma

| | | | | | |
|---|---|---|---|---|---|
| M. hyopneumoniae UCD 1 | 0.25 | 5.0 | >10 | >10 | 10 |
| M. hyopneumoniae TAM 6N | 0.25 | 5.0 | >10 | >10 | 10 |
| M. hyopneumoniae ATCC 25095 | 0.25 | 5.0 | >10 | >10 | 5.0 |
| M. hyopneumoniae NCTC 101101 | 0.25 | 5.0 | >10 | >10 | 10 |
| M. hyorhinis ATCC 23234 | 0.1 | 5.0 | >10 | >10 | 5.0 |
| M. hyorhinis ATCC 25021 | 0.1 | 2.5 | >10 | >10 | 2.5 |
| M. hyosynoviae ATCC 25591 | 0.5 | 2.5 | >10 | >10 | 10 |
| M. bovis NCTC 10131 | 0.05 | 0.1 | 1.0 | 5.0 | 0.1 |
| M. bovigenitalium ATCC 14173 | 0.1 | NG | 5.0 | 10 | 0.5 |
| M. dispar NCTC 10125 | 0.05 | 1.0 | >10 | 10 | 2.5 |
| M. gallisepticum S6 | >10 | >10 | >10 | >10 | >10 |
| M. pneumoniae ATCC 15492 | >10 | >10 | >10 | >10 | >10 |

| | Compound of Example No | |
|---|---|---|
| Organism | 16 | 17* |
| M. hyopneumoniae NB12 | NG | NG |
| M. hyopneumoniae JF 435 | 1.0 | 5.0 |
| M. hyopneumoniae HK (2) | 0.5 | 2.5 |
| M. hyopneumoniae Str. 11 | 0.25 | 1.0 |
| M. hyopneumoniae J2206/183[b] | 0.5 | 2.5 |
| M. hyopneumoniae MS 16 | NG | 1.0 |
| M. hyopneumoniae PW/C/210 | NG | NG |
| M. hyopneumoniae LABER | 0.25 | 2.5 |
| M. hyopneumoniae UCD 1 | 0.5 | 2.5 |
| M. hyopneumoniae TAM 6N | 1.0 | 2.5 |
| M. hyopneumoniae ATCC 25095 | 0.1 | 1.0 |
| M. hyopneumoniae NCTC 101101 | 1.0 | 2.5 |
| M. hyorhinis ATCC 23234 | 0.25 | 2.5 |
| M. hyorhinis ATCC 25021 | 0.25 | 2.5 |
| M. hyosynoviae ATCC 25591 | 5.0 | 1.0 |
| M. bovis NCTC 10131 | 0.25 | 0.05 |
| M. bovigenitalium ATCC 14173 | 0.5 | 0.1 |
| M. dispar NCTC 10125 | 0.1 | 0.5 |
| M. gallisepticum S6 | >10 | 10 |
| M. pneumoniae ATCC 15492 | >10 | >10 |

*only the E isomer was tested.

TABLE 2

MIC's (μg/ml) against Veterinary Bacteria

| | Compound of Example No. | | | | |
|---|---|---|---|---|---|
| Organism | 1 | 2 | 3 | 4 | 5 |
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | >80 | >80 | >80 | >80 | >80 |
| Bord. bronchiseptica B09 | 40 | 80 | 5.0 | 10 | 20 |
| Past. multocida PA1 | 10 | 2.5 | 2.5 | 2.5 | 1.25 |
| Past. multocida PA2 | 1.25 | 1.25 | 2.5 | 1.25 | 1.25 |
| Past. haemolytica PA5 | 10 | 10 | 20 | 20 | C |
| Erysipelothrix rhusiopathiae NCTC 8163 | 80 | 40 | 40 | 40 | 80 |
| Corynebacterium pyogenes CY1 | >80 | .>80 | >80 | >80 | >80 |
| Staph. aureus B4 (pen. resistant) | 5.0 | 5.0 | 2.5 | 5.0 | 10 |
| Staph. aureus 152 (pen. sens) | 5.0 | 10 | 2.5 | 5.0 | 10 |
| Staph. aureus Oxford | 5.0 | 20 | 5.0 | 10 | 20 |
| Strep. suis (group D) SPS11 | 80 | >80 | 80 | 80 | >80 |
| Strep. uberis SPU1 | 5.0 | 2.5 | 2.5 | 2.5 | 2.5 |
| Strep. dysgalactiae SPD1 | 10 | 5.0 | 10 | 10 | 10 |
| Strep. agalactiae SPA1 | 40 | 10 | 10 | 10 | 20 |
| B. subtilis ATCC 6633 | | | NT | 5.0 | 2.5 |

| | Compound of Example No. | | | |
|---|---|---|---|---|
| Organism | 6 | 7 | 8 | 9 |
| E. coli NCTC 10418 | >80 | >80 | >80 | >80 |
| E. coli E1 | >80 | >80 | >80 | >80 |
| S. dublin S7 | >80 | >80 | >80 | >80 |
| S. typhimurium S18 | >80 | >80 | >80 | >80 |
| Bord. bronchiseptica B08 | >80 | >80 | >80 | >80 |
| Bord. bronchiseptica B09 | 80 | 20 | 80 | >80 |
| Past. multocida PA1 | 2.5 | 2.5 | 1.25 | 40 |
| Past. multocida PA2 | NG | 0.625 | 0.625 | 80 |
| Past. haemolytica PA5 | 20 | 20 | 40 | 40 |
| Erysipelothrix rhusiopathiae NCTC 8163 | 80 | 80 | >80 | >80 |

TABLE 2-continued

MIC's (µg/ml) against Veterinary Bacteria

| Organism | | | | |
|---|---|---|---|---|
| Corynebacterium pyogenes CY1 | >80 | >80 | >80 | >80 |
| Staph. aureus B4 (pen. resistant) | 2.5 | 10 | 20 | 80 |
| Staph. aureus 152 (pen. sens) | 5.0 | 10 | 40 | 80 |
| Staph. aureus Oxford | 10 | >80 | 80 | |
| Strep. suis (group D) SPS11 | 80 | >80 | >80 | >80 |
| Strep. uberis SPU1 | 5.0 | 2.5 | 10 | 80 |
| Strep. dysgalactiae SPD1 | 40 | 10 | 40 | >80 |
| Strep. agalactiae SPA1 | 40 | 20 | >80 | >80 |
| B. subtilis ATCC 6633 | NT | 2.5 | 10 | NG |

| | Compound of Example No. | | | |
|---|---|---|---|---|
| Organism | 10 | 11 | 12 | 13 |
| E. coli NCTC 10418 | >80 | >80 | >80 | >80 |
| E. coli E1 | >80 | >80 | >80 | >80 |
| S. dublin S7 | >80 | >80 | >80 | >80 |
| S. typhimurium S18 | >80 | >80 | >80 | >80 |
| Bord. bronchiseptica B08 | >80 | >80 | >80 | >80 |
| Bord. bronchiseptica B09 | >80 | 40 | >80 | 80 |
| Past. multocida PA1 | 40 | 2.5 | >80 | 40 |
| Past. multocida PA2 | 5.0 | 0.312 | >80 | 5.0 |
| Past. haemolytica PA5 | 40 | 10 | >80 | >80 |
| Erysipelothrix rhusiopathiae NCTC 8163 | 40 | 40 | >80 | >80 |
| Corynebacterium pyogenes CY1 | >80 | >80 | >80 | >80 |
| Staph. aureus B4 (pen. resistant) | 5.0 | 20 | >80 | >80 |
| Staph. aureus 152 (pen. sens) | 5.0 | 20 | >80 | 20 |
| Staph. aureus Oxford | 20 | 5.0 | >80 | 40 |
| Strep. suis (group D) SPS11 | >80 | >80 | >80 | >80 |
| Strep. uberis SPU1 | 20 | 2.5 | 80 | 40 |
| Strep. dysgalactiae SPD1 | 80 | 2.5 | >80 | >80 |
| Strep. agalactiae SPA1 | >80 | 5.0 | >80 | >80 |
| B. subtilis ATCC 6633 | 5.0 | 2.5 | NG | NG |

| | Compound of Example No. | | | |
|---|---|---|---|---|
| Organism | 14 | *15 | 16 | *17 |
| E. coli NCTC 10418 | >80 | >80 | >80 | >80 |
| E. coli E1 | >80 | >80 | >80 | >80 |
| S. dublin S7 | >80 | >80 | >80 | >80 |
| S. typhimurium S18 | >80 | >80 | >80 | >80 |
| Bord. bronchiseptica B08 | >80 | >80 | 80 | >80 |
| Bord. bronchiseptica B09 | >80 | 80 | 10 | 40 |
| Past. multocida PA1 | 80 | 40 | 5.0 | 2.5 |
| Past. multocida PA2 | 1.25 | NT | NG | NG |
| Past. haemolytica PA5 | >80 | >80 | 20 | 80 |
| Erysipelothrix rhusiopathiae NCTC 8163 | >80 | 40 | 10 | 10 |
| Corynebacterium pyogenes CY1 | >80 | >80 | >80 | >80 |
| Staph. aureus B4 (pen. resistant) | >80 | 5.0 | 1.25 | 1.25 |
| Staph. aureus 152 (pen. sens) | >80 | 5.0 | 2.5 | 1.25 |
| Staph. aureus Oxford | >80 | 40 | 2.5 | 2.5 |
| Strep. suis (group D) SPS11 | >80 | >80 | 80 | 20 |
| Strep. uberis SPU1 | >80 | 2.5 | 2.5 | 0.625 |
| Strep. dysgalactiae SPD1 | >80 | 10 | 10 | 2.5 |
| Strep. agalactiae SPA1 | >80 | NT | 5.0 | 5.0 |
| B. subtilis ATCC 6633 | NG | NG | 2.5 | 0.625 |

*Only the E-isomer was tested

TABLE 3

MIC's (µg/ml) against Human Bacteria

| | Compound of Example No. | | | | | |
|---|---|---|---|---|---|---|
| Organism | 1 | 2 | 3 | 4 | 5 | 6 |
| E. coli NCTC 10418 | >100 | >128 | >128 | >64 | >128 | >128 |
| E. coli ESS | 10 | 4.0 | 4.0 | 4.0 | 4.0 | 8.0 |
| P. mirabilis 889 | >100 | >128 | >128 | >64 | >128 | >128 |
| K. aerogenes A | >100 | >128 | >128 | >64 | >128 | >128 |
| Ps. aeruginosa NCTC 10662 | >100 | >128 | >128 | >64 | >128 | >128 |
| Pasteurella multocida 1633 | 2.5 | 2.0 | 8.0 | 4.0 | 1.0 | 2.0 |
| Haemophilus influenzae Q1 | 2.5 | NG | C | C | C | C |
| Haemophilus influenzae Wy21 | 2.5 | 0.5 | 2.0 | 1.0 | 0.5 | 2.0 |
| Neisseria catarrhalis 1502 | 2.5 | 0.5 | C | C | C | C |
| Bacillus subtilis 6633 | 5.0 | 4.0 | 4.0 | 16 | 4.0 | 4.0 |

TABLE 3-continued

MIC's (μg/ml) against Human Bacteria

| | | | | | | |
|---|---|---|---|---|---|---|
| Corynebacterium xerosis 9755 | >100 | >128 | >128 | >64 | >128 | 128 |
| Sarcina lutea 8340 | >100 | NG | >128 | >64 | >128 | 32 |
| Staph. aureus Oxford | 10 | 16 | 8.0 | 8.0 | 8.0 | 8.0 |
| Staph. aureus Russell | 25 | 64 | 8.0 | 32 | 32 | 16 |
| Staph. aureus W2827 | 25 | 64 | 8.0 | 32 | 32 | 16 |
| Strep. faecalis I | >100 | >128 | >128 | >64 | >128 | >128 |
| Strep. pyogenes R80/421-A | 100 | 4.0 | 16 | 16 | 8.0 | 16 |
| Strep. agalactiae 2788-B | 100 | 32 | 32 | 16 | 32 | 32 |
| Strep. spp. 64/848-C | 25 | 32 | 16 | 16 | 32 | 32 |
| Strep. pneumoniae CN33 | 100 | 32 | NG | NG | NG | NG |

| | Compound of Example No. | | | |
|---|---|---|---|---|
| Organism | 7 | 8 | 9 | 10 |
| E. coli NCTC 10418 | >128 | >128 | >100 | >128 |
| E. coli ESS | 64 | 8.0 | ≧100 | 2.0 |
| P. mirabilis 889 | NG | >128 | ≧100 | >128 |
| K. aerogenes A | 128 | >128 | >100 | >128 |
| Ps. aeruginosa NCTC 10662 | >128 | >128 | >100 | >128 |
| Pasteurella multocida 1633 | >128 | 1.0 | 10 | 16 |
| Haemophilus influenzae Q1 | NG | NG | 2.5 | NG |
| Haemophilus influenzae Wy21 | 1.0 | 0.25 | 2.5 | 2.0 |
| Neisseria catarrhalis 1502 | 0.25 | 0.5 | 2.5 | 0.5 |
| Bacillus subtilis 6633 | 2.0 | 4.0 | ≧100 | 2.0 |
| Corynebacterium xerosis 9755 | NG | NG | >100 | NG |
| Sarcina lutea 8340 | >128 | >128 | >100 | >128 |
| Staph. aureus Oxford | 2.0 | 4.0 | 100 | 1.0 |
| Staph. aureus Russell | 32 | 64 | ≧100 | 4.0 |
| Staph. aureus W2827 | 32 | 32 | ≧100 | 4.0 |
| Strep. faecalis I | >128 | >128 | >100 | >128 |
| Strep. pyogenes R80/421-A | NG | NG | 100 | NG |
| Strep. agalactiae 2788-B | 8.0 | 32 | ≧100 | 16 |
| Strep. spp. 64/848-C | 8.0 | 32 | ≧100 | 16 |
| Strep. pneumoniae CN33 | NG | NG | ≧100 | NG |

| | Compound of Example No. | | | |
|---|---|---|---|---|
| Organism | 11 | 12 | 13 | 14 |
| E. coli NCTC 10418 | >64 | >100 | >64 | >128 |
| E. coli ESS | 2.0 | 100 | >64 | >128 |
| P. mir | >64 | >100 | >64 | >128 |
| K. aerogenes A | >64 | >100 | >64 | >128 |
| Ps. aeruginosa NCTC 10662 | >64 | >100 | >64 | >128 |
| Pasteurella multocida 1633 | 2.0 | 5.0 | 64 | 64 |
| Haemophilus influenzae Q1 | NG | 1.0 | NG | NG |
| Haemophilus influenzae Wy21 | 0.5 | 2.5 | 16 | 128 |
| Neisseria catarrhalis 1502 | 0.25 | 10 | 64 | >128 |
| Bacillus subtilis 6633 | 2.0 | 100 | >64 | >128 |
| Corynebacterium xerosis 9755 | NG | ≧100 | >64 | >128 |
| Sarcina lutea 8340 | >64 | ≧100 | NG | NG |
| Staph. aureus Oxford | 8.0 | 100 | >64 | >128 |
| Staph. aureus Russell | 32 | ≧100 | >64 | >128 |
| Staph. aureus W2827 | 16 | 100 | >64 | >128 |
| Strep. faecalis I | >64 | >100 | >64 >128 | |
| Strep. pyogenes R80/421-A | NG | 50 | >64 | >128 |
| Strep. agalactiae 2788-B | 2.0 | 50 | >64 | >128 |
| Strep. spp. 64/848-C | 2.0 | 100 | >64 | >128 |
| Strep. pneumoniae CN33 | NG | 100 | >64 | >128 |
| | | | >64 | >128 |

| | Compound of Example No. | | |
|---|---|---|---|
| Organism | *15 | 16 | *17 |
| E. coli NCTC 10418 | >128 | >64 | >128 |
| E. coli ESS | 8.0 | 8.0 | 4.0 |
| P. mirabilis 889 | >128 | >64 | >128 |
| K. aerogenes A | >128 | >64 | >128 |
| Ps. aeruginosa NCTC 10662 | >128 | >64 | >128 |
| Pasteurella multocida 1633 | 64 | 32 | 16 |
| Haemophilus influenzae Q1 | C | C | C |
| Haemophilus influenzae Wy21 | 4.0 | 4.0 | 1.0 |
| Neisseria catarrhalis 1502 | C | C | C |
| Bacillus subtilis 6633 | 32 | 16 | 2.0 |
| Corynebacterium xerosis 9755 | >128 | >64 | >128 |
| Sarcina lutea 8340 | >128 | >64 | >128 |
| Staph. aureus Oxford | 16 | 16 | 4.0 |
| Staph. aureus Russell | 32 | 16 | 4.0 |
| Staph. ureus W2827 | 32 | 16 | 4.0 |
| Strep. faecalis I | >128 | >64 | >128 |
| Strep. pyogenes R80/421-A | 32 | 32 | 4.0 |
| Strep. agalactiae 2788-B | 64 | 32 | 8.0 |
| Strep. spp. 64/848-C | 64 | 32 | 8.0 |

TABLE 3-continued

| MIC's (μg/ml) against Human Bacteria | | | |
| --- | --- | --- | --- |
| Strep. pneumoniae CN33 | NG | NG | C |

*Only the E-isomer was tested

We claim:

1. A compound of formula (I):

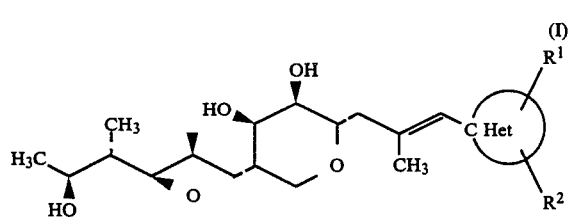

wherein

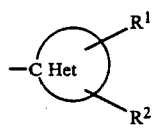

is a tri-valent, 5-membered heterocyclic group having a 6-π electron system, the five ring atoms being
two carbon atoms, two nitrogen atoms and one atom selected from oxygen and sulphur,
and $R^1$ is a substitutent on a carbon or nitrogen of

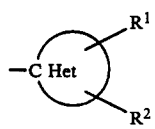

selected from $C_{1-20}$ alkyl, $C_{2-8}$ alkenyl, phenyl, $C_{1-4}$ alkylene) phenyl and a 5 or 6 membered heterocyclic ring having from 1 to 3 heteroatoms each selected from oxygen, nitrogen and sulphur, each of which may be substituted or unsubstituted; hydrogen and $C_{3-7}$ cycloalkyl, and, where appropriate, $R^2$ is a substituent on a carbon or nitrogen of

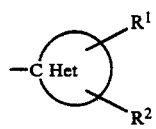

and when present is the same or different than $R^1$ and is selected from $C_{1-20}$ alkyl, $C_{2-8}$ alkenyl, phenyl, $(C_{1-4}$ alkylene) phenyl and a 5 or 6 membered heterocyclic ring having from 1 to 3 heteroatoms each selected from oxygen, nitrogen and sulphur, each of which may be substituted or unsubstituted; hydrogen and $C_{3-7}$ cycloalkyl; and wherein, when either of $R^1$ or $R^2$ is a $C_{1-20}$ alkyl or $C_{2-8}$ alkenyl group, it may be substituted with up to two substituents selected from the group consisting of: halogen, carboxy, $C_{1-6}$ alkoxy-carbonyl, carbamoyl, mono- or di-$(C_{1-6})$ alkylcarbamoyl, sulphamoyl, mono- and di-$(C_{1-6})$ alkylsulphamoyl, amino, mono- and di-$(C_{1-6})$ alkylamino, $C_{1-6}$ acylamino, ureido, $C_{1-6}$ alkoxycarbonylamino, 2,2,2-trichloroethoxy-carbonylamino, phenyl, a 5 or 6 membered heterocyclic ring containing from 1 to 3 heteroatoms each selected from oxygen, nitrogen and sulphur, hydroxy, $C_{1-6}$ alkoxy, oxo, aroyl, 2-thenoyl, $C_{1-6}$ alkylthio, $C_{1-6}$ alkanesulphinyl, $C_{1-6}$ alkanesulphonyl, hydroxyimino, hydrazono, benzohydroximoyl, 2-thiophenecarbohydroximoyl; when either of $R^1$ or $R^2$ is a phenyl, $(C_{1-4}$ alkylene) phenyl or a 5 or 6 membered heterocyclic ring containing from 1 to 3 heteroatoms each selected from oxygen, nitrogen and sulphur, the phenyl and heterocyclic moieties may be substituted with up to two substituents selected from the group consisting of: halogen, $C_{1-6}$ alkyl, $C_{1-6}$ alkoxy, hydroxy, carboxy, $C_{1-6}$ alkoxycarbonyl, carbamoyl, mono- or di-$(C_{1-6})$ alkyl carbamoyl, sulfamoyl, mono- and di-$(C_{1-6})$alkysulfamsyl, cyano, nitro, amino, mono- and di-$(C_{1-6})$ alkylamino, $(C_{1-6})$ acylamino, ureido, $C_{1-6}$ alkoxycarbonylamino, 2,2,2-trichloroethoxycarbonylamino, $C_{1-6}$ alkanoyl, $C_{1-6}$ alkylthio, $C_{1-6}$ alkanesulphinyl, and $C_{1-6}$ alkanesulphonyl.

2. A compound according to claim 1 having the formula (IA)

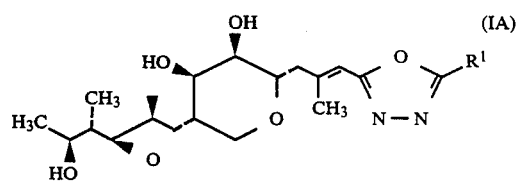

wherein $R^1$ is as defined in claim 1.

3. A compound according to claim 1 and having the formula (IC)

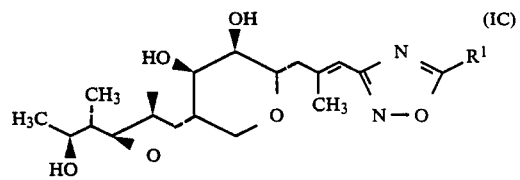

wherein $R^1$ is as defined in claim 1.

4. A compound according to claim 1 and having the formula (ID)

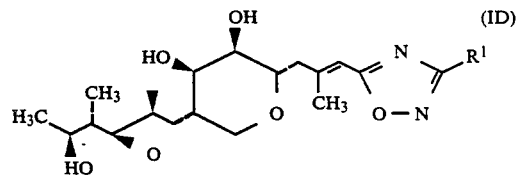

wherein $R^1$ is as defined in claim 1.

5. A compound according to claim 1 and selected from 2-(1-Normon-2-yl)-5-phenyl-1,3,4-oxadiazole A;
2-m-Nitrophenyl-5-(1-normon-2-yl)-1,3,4-oxadiazole A;
2-p-Methylthiophenyl-5-(1-normon-2-yl)-1,3,4-oxadiazole A;

2-p-Methylsulphonylphenyl-5-(1-normon-2-yl)-1,3,4-oxadiazole A;
2-(1-Normon-2-yl)-5-(3-pyridyl)-1,3,4-oxidiazole A;
2-(1-Normon-2-yl)-5-(2-thienyl)-1,3,4-oxadiazole A;
2-(1-Normon-2-yl)-5-(4-pyridyl)-1,3,4-oxidiazole A;
2-(2-Furyl)-5-(1-normon-2-yl)-1,3,4-oxadiazole A;
2-(4-Dimethylaminophenyl)-5-(1-normon-2-yl)-1,3,4-oxadiazole A;
2-(m-Cyanophenyl)-5-(1-normon-2-yl)-1,3,4-oxadiazole A;
5-(1-Normon-2-yl)-3-phenyl-1,2,4-oxadiazole A;
5-(1-Normon-2-yl)-3-(4-nitrophenyl)-1,2,4-oxadiazole and
3-(1-Normon-2-yl)-5-phenyl-1,2,4-oxidiazole.

6. A pharmaceutical or veterinary composition for treating mycoplasmal or bacterial infections in human and non-human animals which comprises a pharmaceutically or veterinarily effective amount of a compound of formula (I), as defined in claim 1, and a pharmaceutically or veterinarily acceptable carrier or excipient.

7. A method for treating mycoplasmal or bacterial infections in human and non-human animals comprising administering an effective non-toxic amount of a compound of formula (I) according to claim 1 to the sufferer.

* * * * *